US008248586B2

(12) United States Patent
Tomita

(10) Patent No.: US 8,248,586 B2
(45) Date of Patent: Aug. 21, 2012

(54) BLOOD ANALYSIS APPARATUS AND SETTING METHOD OF MEASUREMENT POSITION IN BLOOD ANALYSIS APPARATUS

(75) Inventor: Mamoru Tomita, Himeji (JP)

(73) Assignee: Rohm Co., Ltd., Kyoto-shi, Kyoto (JP)

( * ) Notice: Subject to any disclaimer, the term of this patent is extended or adjusted under 35 U.S.C. 154(b) by 374 days.

(21) Appl. No.: 12/427,280

(22) Filed: Apr. 21, 2009

(65) Prior Publication Data
US 2009/0268194 A1    Oct. 29, 2009

(30) Foreign Application Priority Data

Apr. 24, 2008    (JP) .............................. P2008-113584

(51) Int. Cl.
*G01N 33/48*    (2006.01)
*G01N 21/00*    (2006.01)
*G01B 11/00*    (2006.01)
*G01B 11/14*    (2006.01)

(52) U.S. Cl. .......... 356/39; 356/399; 356/432; 356/440; 356/614; 422/82.09; 436/164

(58) Field of Classification Search ........................ None
See application file for complete search history.

(56) References Cited

U.S. PATENT DOCUMENTS

2007/0280854 A1    12/2007    Matsumoto et al.
2008/0002178 A1*    1/2008    Ogawa et al. .................. 356/39

FOREIGN PATENT DOCUMENTS

| CN | 101082621 | 12/2007 |
| CN | 101097184 | 1/2008 |
| JP | 2006-110491 | 4/2006 |
| JP | 2007-322208 | 12/2007 |

* cited by examiner

*Primary Examiner* — Tarifur Chowdhury
*Assistant Examiner* — Gordon Stock, Jr.
(74) *Attorney, Agent, or Firm* — Drinker Biddle & Reath LLP

(57) ABSTRACT

A blood analysis apparatus is provided. The blood analysis apparatus includes: a chip holding portion having an aperture which allows light to pass therethrough and holding a μ-TAS chip for holding a measurement liquid; a rotary body on which the chip holding portion is mounted; a light source; and a light-receiving unit. A measurement position of the rotary body at which the measurement liquid is to be measured with the light from the light source is set by: rotating the rotary body to obtain a light value of light which is emitted from the light source and received by the light-receiving unit through the aperture; and setting a rotational position of the rotary body where the light value is a threshold value or more, as the measurement position.

7 Claims, 18 Drawing Sheets

BLOOD ANALYSIS APPARATUS AND SETTING METHOD OF MEASUREMENT POSITION IN BLOOD ANALYSIS APPARATUS

This application claims priority from Japanese Patent Application No. 2008-113584, filed on Apr. 24, 2008, the entire contents of which are hereby incorporated by reference.

BACKGROUND OF THE INVENTION

1. Technical Field

The present disclosure relates to a blood analysis apparatus which centrifugally rotates a μ-TAS (Micro-Total Analysis System) chip for holding a sample, such as blood, and measures a measurement liquid held by the μ-TAS chip by an absorbance analysis method, and a setting method of a measurement position in the blood analysis apparatus. More particularly, the present disclosure relates to a blood analysis apparatus and a setting method of a measurement position in the blood analysis apparatus, which can exactly set the measurement position when the absorbance measurement of the measurement liquid held by the μ-TAS chip is performed.

2. Related Art

In recent years, attention is paid to an analytical method utilizing a μ-TAS chip, called "μ-TAS" or "Lab on a chip", capable of applying a micro-machine technique and performing chemical analysis or the like in a finer manner as compared with a conventional apparatus.

The analyzing system (hereinafter referred to as "μ-TAS chip analyzing system") using such a μ-TAS chip is a system which aims to perform all the steps of analysis including mixing, reaction, separation, extraction, and detection of a reagent in a fine flow passage formed on a small base through a micro-machine manufacturing technique, and is used for, for example, analysis of blood, and analysis of biomolecule, such as an ultratrace amount of protein or nucleic acid, in a medical field.

Particularly, when people's blood is analyzed using the μ-TAS chip analyzing system, the following advantages are obtained. Therefore, in recent years, development is positively moving forward.

(1) Since the amount of blood (sample) which is required for analytical inspection is slight amount, a burden to a patient can be mitigated.

(2) Since the amount of a reagent which is used while being mixed with blood is small, analysis cost can be reduced.

(3) Since the apparatus itself can be configured as a small one, analysis can be easily performed.

In such a μ-TAS chip analyzing system, for example, absorptiometry is used as a method for measuring the concentration of a component of an object to be detected in a measurement liquid (sample liquid). For example, JP-A-2007-322208 describes a blood analysis apparatus using the absorptiometry.

A configuration example of a measuring unit in the blood analysis apparatus is shown in FIG. 18. FIG. 18 is a schematic cross-sectional view showing the internal structure of the measuring unit in the blood analysis apparatus.

The blood analysis apparatus include a casing (not shown), and the inside of the casing is provided with a measuring unit 20, a light source unit having a light source 41, a light-receiving unit 43 (shown in FIG. 18), a controller, a power supply unit (not shown), and the like.

The measuring unit 20, as shown in FIG. 18, has a hollow columnar measuring chamber 21, and, for example, a cylindrical rotary body 25 having a bottom surface is arranged in the measuring chamber 21. A driving shaft 24b is arranged so as to extend in a vertical direction through a central position of the bottom surface of the rotary body 25, and the driving shaft 24b is connected to a centrifugal motor 24a. As the centrifugal motor 24a is driven, the rotary body 25 is rotationally driven.

The centrifugal motor 24a, the driving shaft 24b, and an encoder 24c (described later) constitute a rotation driving mechanism 24.

The bottom of the rotary body 25 is provided with a direction switching gear 26 whose external diameter is smaller than the radius of the rotary body 25, the direction switching gear 26 is rotatably supported around a shaft D which is located on the rotary body 25 and is parallel to the rotation center C thereof, and a chip holding portion 22 for holding a μ-TAS chip 60 is provided on the gear 26. The chip holding portion 22 is arranged so as to be located in an outer peripheral area of the rotary body 25.

In addition, the measuring unit 20 can be configured so as to have a plurality of the chip holding portions 22. In FIG. 18, in order to maintain the rotation balance of the rotary body 25 in a proper state, the chip holding portions 22 of the same configuration are provided in opposite positions with the rotation center C therebetween.

A light-introducing opening 22a and an aperture 23 which introduce the light incident via a reflecting mirror 42 from the light source 41 into a measuring area of the μ-TAS chip 60 are each formed at a lower portion of the measuring chamber 21, the rotary body 25, and the direction switching gear 26 provided with the chip holding portion 22, in a state that the μ-TAS chip 60 is held by the chip holding portion 22. A light-receiving unit 43 which receives this light which has passed through a measuring area of the μ-TAS chip 60 and an opening 22b in which an optical fiber 44 which guides the light is provided are provided in an upper portion of the measuring chamber 21.

When absorbance measurement of a measurement liquid within the measuring area of the μ-TAS chip 60 is performed, this measurement is performed in a state where the rotation of the rotary body 25 has been stopped, and it is necessary to introduce the light from the light source 41 into the measuring area of the μ-TAS chip 60. Accordingly, the stop position of the rotary body 25 must be controlled with high precision of position.

For this reason, the encoder 24c is connected to the centrifugal motor 24a for rotationally driving the rotary body 25, and the stop position of the rotary body 25 is controlled on the basis of a signal from the encoder 24c.

Additionally, a planar heating means (heater) 35 for maintaining the temperature within the measuring chamber 21 at a constant temperature, for example, 37° C., at the time of analytical inspection, is provided in some regions of the top and bottom faces of the measuring chamber 21, and the temperature within the measuring chamber is controlled so as to become constant on the basis of the detection temperature by a temperature measuring means 36 such as a thermistor.

Additionally, the measuring unit 20 includes a chip direction switching mechanism 30, having a drive mechanism separate from a drive mechanism 24 which rotationally drives the rotary body 25. The chip direction switching mechanism 30 adjusts the direction of the μ-TAS chip 60 held by the chip holding portion 22.

The chip direction switching mechanism 30 has a driving-side gear 33 and a chip direction switching motor 31. The driving-side gear 33 is rotatably provided with respect to the driving shaft 24b of the centrifugal motor 24a via a ball bearing 32 or the like and meshes with the direction switching gear 26, and the chip direction switching motor 31 is a driving source for rotationally driving the driving-side gear 33.

By driving the chip direction switching motor 31, the driving-side gear 33 rotates, then the direction switching gear 26 which meshes with this gear rotates, and then the chip holding portion 22 rotates. This makes it possible to switch the direction (direction with respect to the rotation center C of the rotary body 25) of the μ-TAS chip 60.

For example, JP-A-2006-110491 describes the concrete structure, operation, etc. of the chip direction change mechanism 30.

Analytical processing of the measurement liquid by the above-described blood analysis apparatus is performed, for example, as follows. A rotary body mounted with the μ-TAS chip by which a sample (blood) is held is rotated, separation treatment which centrifugally separates the sample is performed using a centrifugal force, and a sample liquid obtained by the separation treatment is weighed.

Subsequently, pretreatment operation including mixing reaction treatment, in which the liquid to be measured and a reagent are mixed together to be reacted, and the processing of delivering a measurement liquid obtained by the mixing reaction treatment to a measuring area is performed.

Subsequently, while the rotation of the rotary body 25 is stopped, the light from the light source unit 41 is introduced into the measuring area of the μ-TAS chip 60, and the light transmitted through the measuring area is received by the light-receiving unit. Thereby, the quantity of light absorbed by the measurement liquid within the measuring area is measured.

Meanwhile, the blood analysis apparatus using the μ-TAS chip has a feature that a small amount of blood can also be analyzed. For this reason, the amount of a measurement liquid obtained by centrifugal separation of blood and mixing and reaction of blood with a reagent also becomes small. When absorbance analysis is performed on this measurement liquid, the measuring area where the measurement liquid is arranged in the μ-TAS chip is a minute region of 1.2 mm×1.2 mm, for example.

In order to make concentrated light enter the measuring area to measure the quantity of light transmitted through the measurement liquid, for example, the diameter of the aperture 23 is about 0.6 mm.

On the other hand, the environmental temperature which surrounds the blood analysis apparatus differs in winter and summer. Due to a change according to this environmental temperature, for example, deformation, such as "expansion/contraction" or "deflection", may occur in the rotary body 25. When the rotary body is deformed due to a change in an environmental temperature, the position of the aperture 23 shifts with respect to an optical axis extending from the light source to the light-receiving unit 43.

Since the aperture 23 is a minute through hole with a diameter of φ0.6 mm, the amount of the light which enters the aperture 23 lowers extremely if the rotary body 25 with a diameter of φ170 mm is simply deformed slightly.

In addition, in order to prevent the quantity of light which enters the aperture 23 from lowering extremely, it is conceivable to enlarge the diameter of the aperture 23. However, if the aperture 23 is made larger than the measuring area (area where the measurement liquid is located) of the μ-TAS chip, the light from the light source may enter portions other than the measuring area, and thus it becomes impossible to measure only the quantity of light transmitted through the measurement liquid.

As described above, the problem that test results greatly change due to the deformation of the rotary body 25 has been a problem peculiar to the blood analysis apparatus using the μ-TAS chip which perform analysis with a small quantity of blood.

Particularly, in a case where the μ-TAS chip is heated in order to hold the reagent in the μ-TAS chip, and make the reagent and a sample liquid react with each other within the μ-TAS chip, the rotary body holding the μ-TAS chip is also heated. Thus, there is also a problem in that particularly the deformation of the rotary body 25 becomes large.

SUMMARY OF THE INVENTION

Exemplary embodiments of the present invention address the above disadvantages and other disadvantages not described above. However, the present invention is not required to overcome the disadvantages described above, and thus, an exemplary embodiment of the present invention may not overcome any of the disadvantages described above.

Accordingly, it is an object of the invention to provide a blood analysis apparatus and a setting method of a measurement position in the blood analysis apparatus, which can obtain the quantity of light required for measurement and enables high-precision measurement, even if a rotary body or the like is deformed due to a change in an environmental temperature.

According to one or more aspects of the present invention, a blood analysis apparatus is provided. The blood analysis apparatus comprises: a driving unit comprising: a chip holding portion having an aperture which allows light to pass therethrough and holding a μ-TAS chip for holding a measurement liquid; a rotary body on which the chip holding portion is mounted; a rotation driving mechanism which rotates the rotary body; and a chip direction switching mechanism which changes a direction of the μ-TAS chip with respect to the rotary body; a measuring unit comprising: a light source which allows the light to enter the aperture; and a light-receiving unit which receives the light from the light source; and a controller which controls the rotation driving mechanism, the light source, and the light-receiving unit. The controller comprises a measurement position setting part which determines a measurement position of the rotary body at which the measurement liquid is to be measured with the light from the light source. Before the measurement liquid is measured, the measurement position setting part controls the rotation driving mechanism to rotate the rotary body and sets a rotational position of the rotary body where a light value of the light received by the light-receiving unit through the aperture is a threshold value or more, as the measurement position.

According to one or more aspects of the present invention, in a blood analysis apparatus comprising: a chip holding portion having an aperture which allows light to pass therethrough and holding a μ-TAS chip for holding a measurement liquid; a rotary body on which the chip holding portion is mounted; a light source; and a light-receiving unit, a method of setting a measurement position of the rotary body at which the measurement liquid is to be measured with the light from the light source comprises: (a) rotating the rotary body to obtain a light value of light, said light being emitted from the light source and received by the light-receiving unit through the aperture; and (b) setting a rotational position of the rotary body where the light value is a threshold value or more, as the measurement position.

Other aspects of the invention will be apparent from the following description, the drawings and the claims.

DETAILED DESCRIPTION OF EXEMPLARY EMBODIMENTS OF THE INVENTION

Hereinafter, exemplary embodiments of the present invention will be described with reference to the drawings.

First Embodiment

FIGS. 1A to 4B are views showing the configuration of an apparatus of a first embodiment of the invention.

Figure 1A:
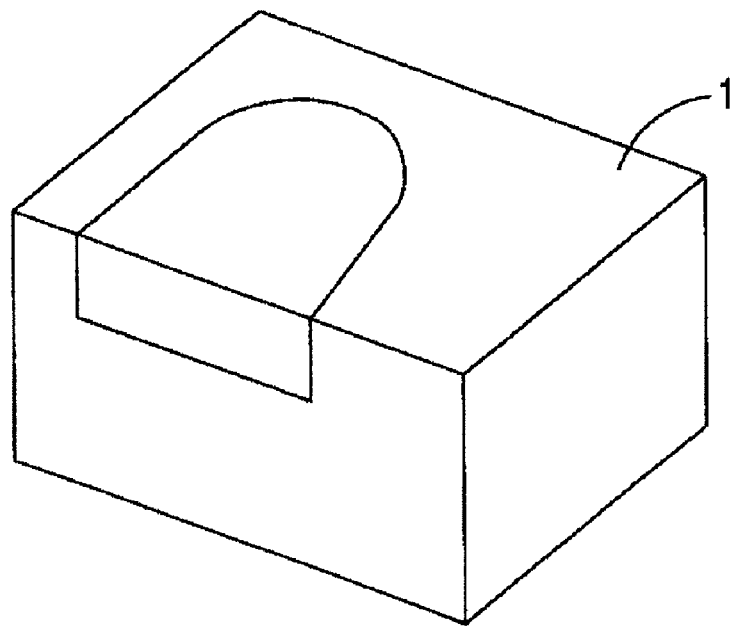
FIGS. 1A and 1B are appearance views of a housing including a blood analysis apparatus according to an exemplary embodiment of the invention.
Figure 1B:
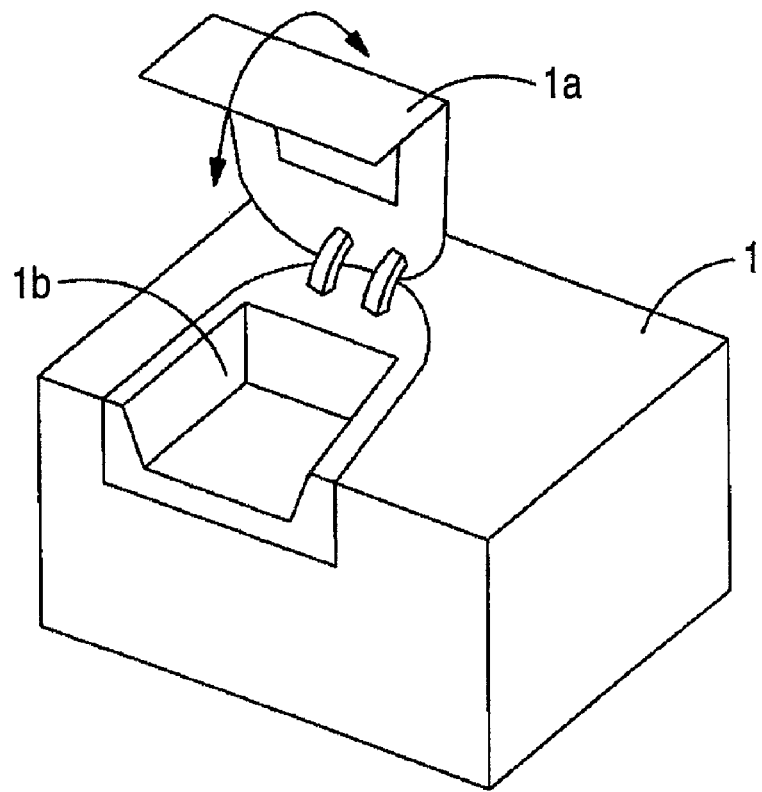

FIGS. 1A and 1B are appearance views of a housing which has a blood analysis apparatus therein, FIG. 1A shows a state where a cover is closed, and FIG. 1B shows a state where the cover is opened and a chip insertion slot of the blood analysis apparatus can be seen.

As shown in FIG. 1A, the blood analysis apparatus is housed in the housing 1, and when a μ-TAS chip is inserted into a blood analysis apparatus, as shown in FIG. 1B, the cover 1a of the housing 1 is opened, and the μ-TAS chip is put into a chip holding portion in a measuring chamber from the chip insertion slot 1b of the measuring chamber.

Figure 2:
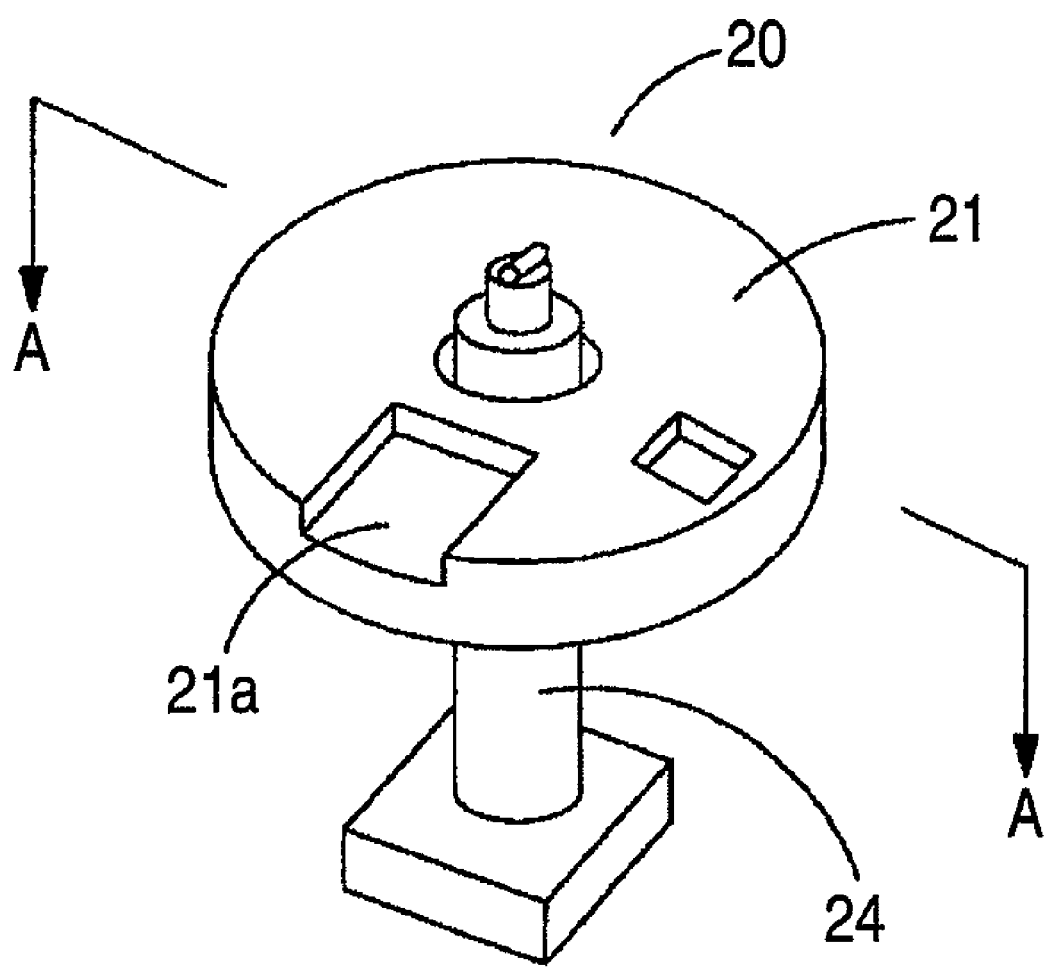
FIG. 2 is a perspective view of a measuring unit of the blood analysis apparatus according the exemplary embodiment to the invention.
Figure 3:
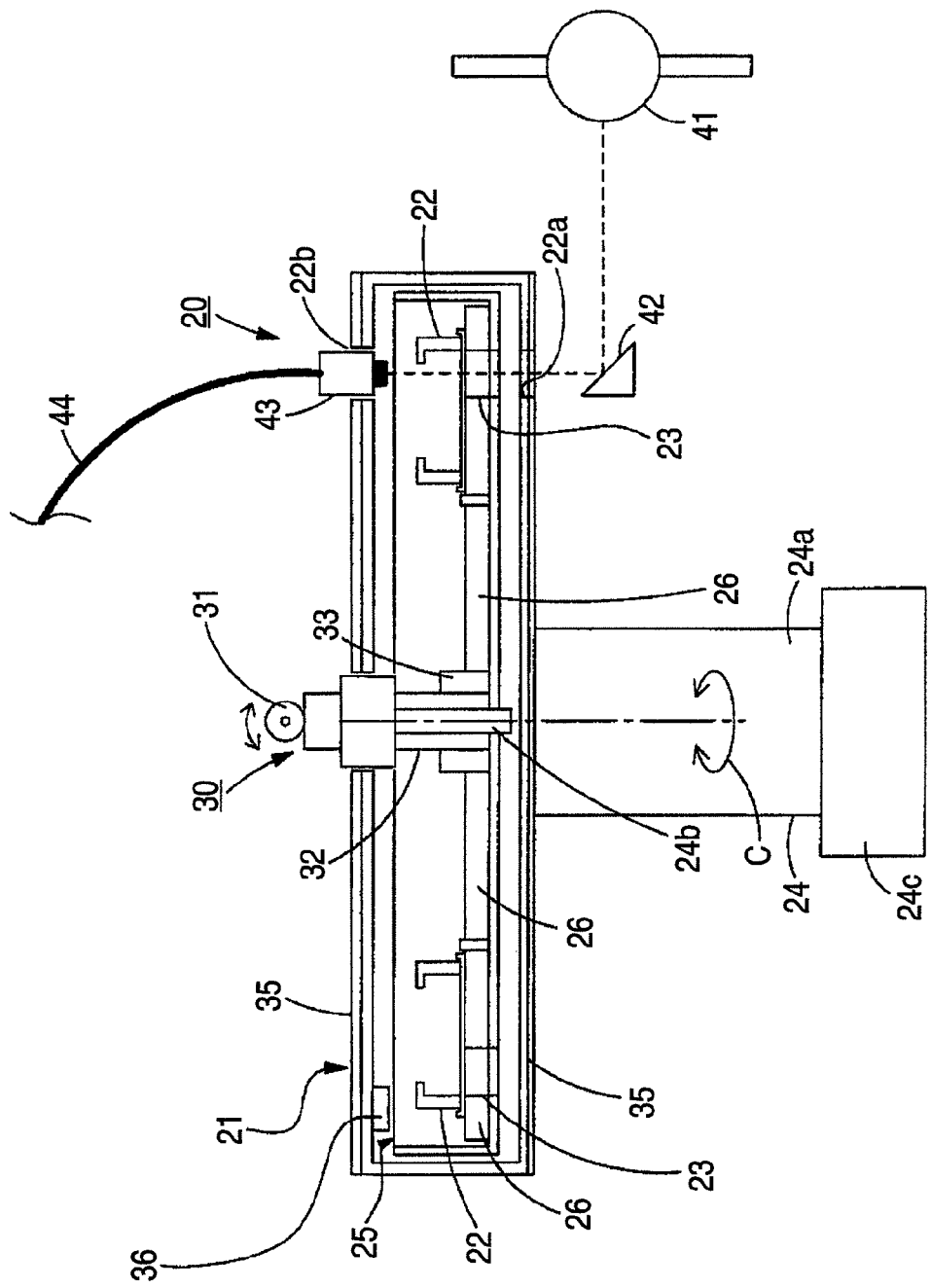
FIG. 3 is a cross-sectional view showing a configuration of the measuring unit of the blood analysis apparatus according to a first embodiment of the invention.

FIGS. 2 and 3 are views showing the configuration of a measuring unit 20 arranged inside the housing 1 of FIG. 1. FIG. 2 is a perspective view of the measuring unit 20, and FIG. 3 is an III-III sectional view of FIG. 2. In addition, an optical fiber, a light-receiving unit, a reflecting mirror, and a light source which are shown in FIG. 3 are omitted in FIG. 2.

As shown in FIG. 2, the measuring unit 20 of the blood analysis apparatus is composed of a measuring chamber 21 which has a rotary body therein, and a rotation driving mechanism 24 which rotationally drives the rotary body, and the measuring chamber 21 is provided with a chip insertion slot 21a for inserting the μ-TAS chip.

Figure 18:
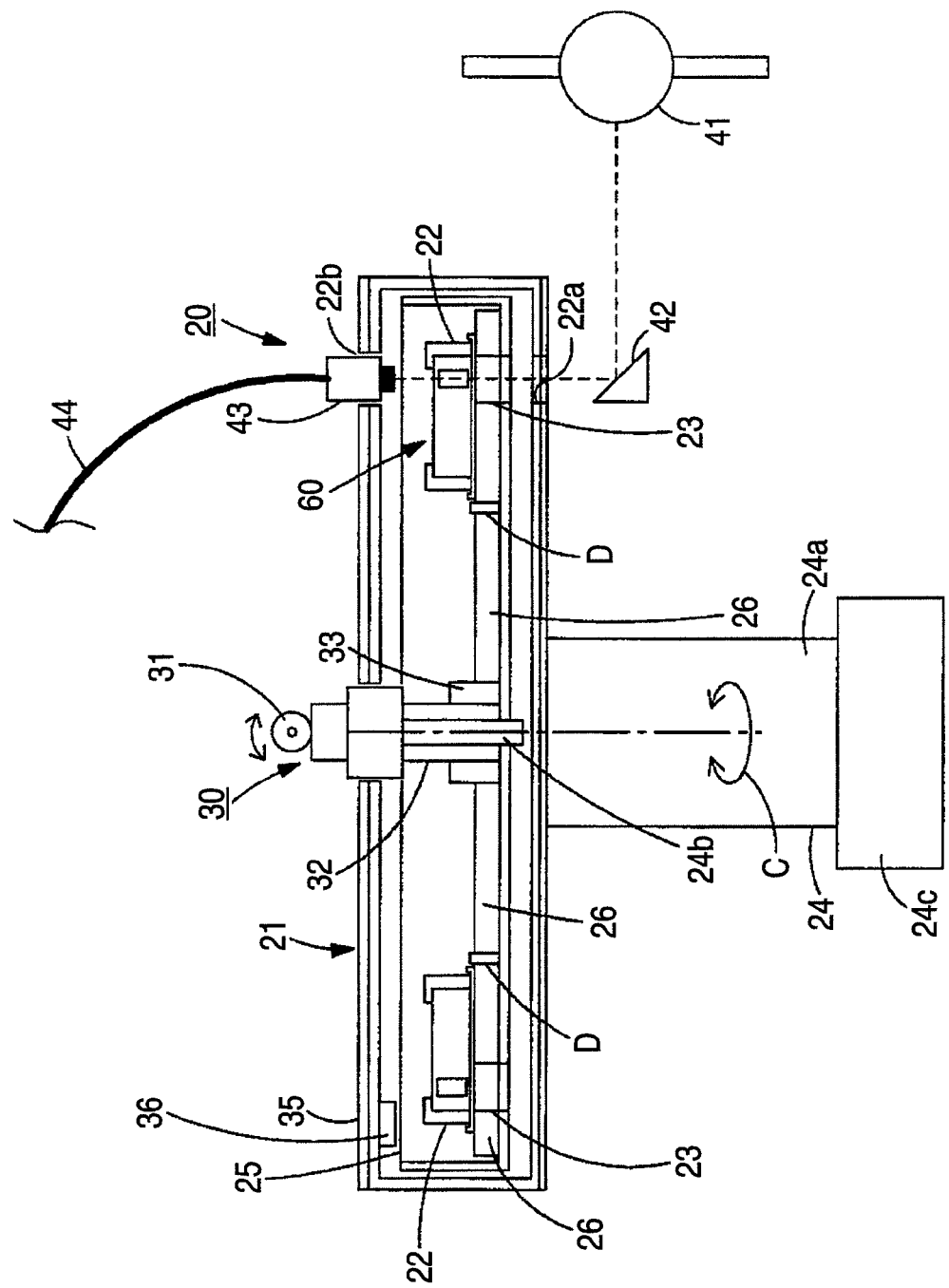
FIG. 18 is a cross-sectional view showing a configuration of a measuring unit of a related-art blood analysis apparatus.

FIG. 3 is a view showing a configuration example of the measuring unit 20 according to the exemplary embodiment, and a basic configuration of the measuring unit is the same as that shown in FIG. 18. In addition, since the step of determining a measurement position in this embodiment is performed before the μ-TAS chip is inserted, the μ-TAS chip is eliminated in FIG. 3.

Since the configuration of FIG. 3 is the same as that shown in FIG. 18, detailed description thereof is omitted here. However, as mentioned above, the measuring unit 20 has a hollow columnar measuring chamber 21, and a rotary body 25 is arranged within the measuring chamber 21. A centrifugal motor 24a of the rotation driving mechanism 24 is connected to a rotary body 25 via a driving shaft 24b, and the rotary body 25 is rotationally driven by the centrifugal motor 24a. Additionally, the centrifugal motor 24a is provided with an encoder 24c for detecting the rotational position of the motor.

As described above, a direction switching gear 26 is rotatably supported and provided at the bottom of the rotary body 25, and the chip holding portion 22 for holding the μ-TAS chip is provided on the gear 26.

The light-introducing opening 22a and the aperture 23 through which the light incident via the reflecting mirror 42 from the light source 41 passes are each formed at a lower portion of the measuring chamber 21, the rotary body 25, and the direction switching gear 26 provided with the chip holding portion 22. The light-receiving unit 43 which receives this light, and the opening 22b in which the optical fiber 44 which guides this light is to be inserted are provided in an upper portion of the measuring chamber 21.

Additionally, a planar heating means 35 for maintaining the temperature within the measuring chamber 21 at a constant temperature, for example, 37° C., is provided in some regions of the top and bottom faces of the measuring chamber 21, and the temperature within the measuring chamber is controlled so as to become constant on the basis of the detection temperature by a temperature measuring means 36 such as a thermistor.

Additionally, the measuring unit 20 includes a chip direction switching mechanism 30 for adjusting the direction of the μ-TAS chip held by the chip holding portion 22 as mentioned above.

By driving the chip direction switching motor 31, the driving-side gear 33 rotates, then the direction switching gear 26 which meshes with this gear rotates, and then the chip holding portion 22 rotates. This makes it possible to switch the direction of the μ-TAS chip 60.

Figure 4A:
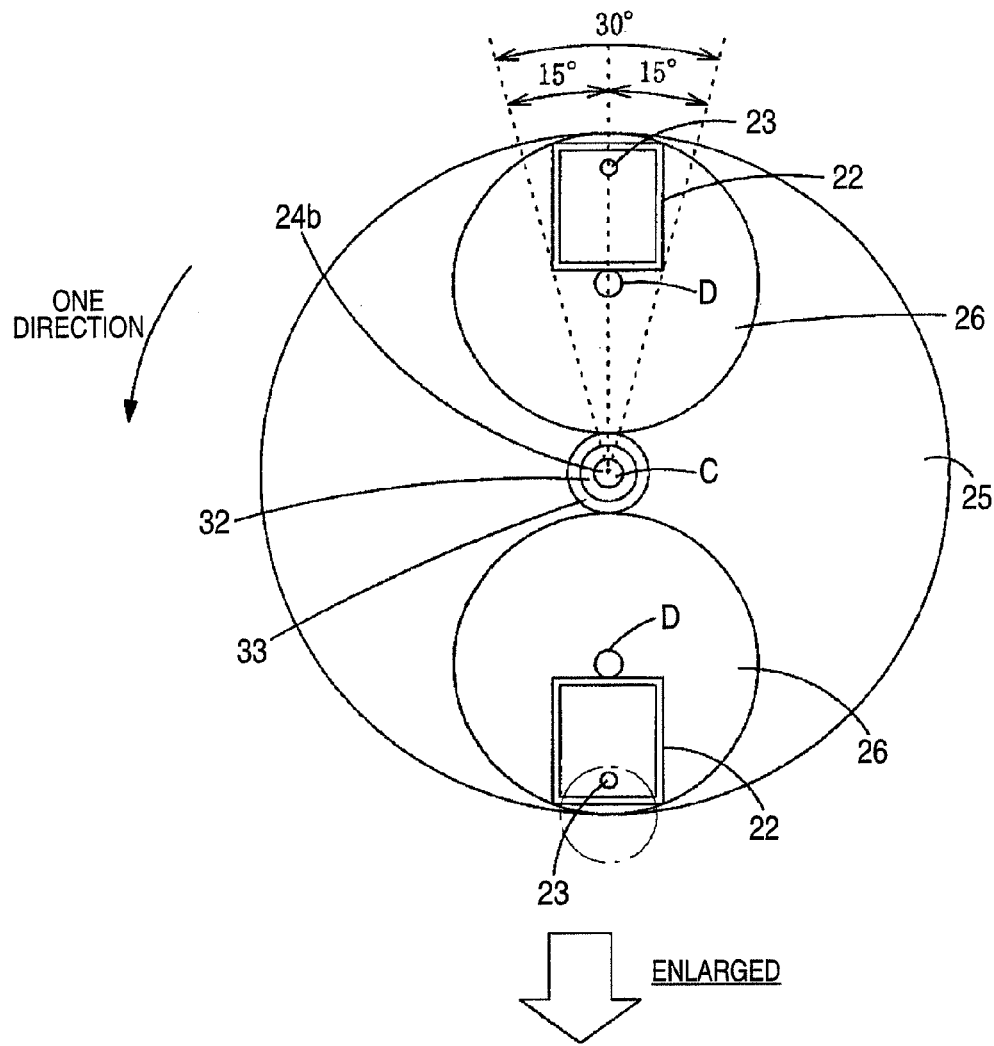
FIGS. 4A and 4B are conceptual diagrams of a rotary body when viewed from a chip holding portion.
Figure 4B:
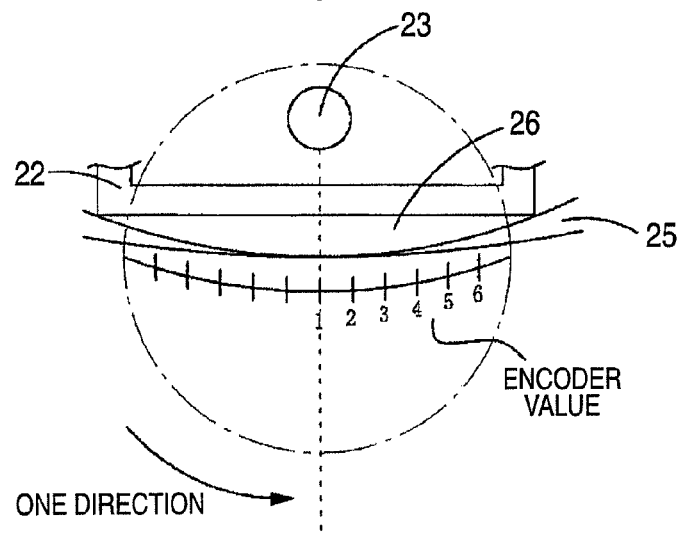

FIG. 4A is a conceptual diagram showing the rotary body 25 when viewed from the chip holding portion, and FIG. 4B is an enlarged view of a region surrounded by a circle of one-dot chain line of FIG. 4A.

As shown in FIG. 4A, the direction switching gear 26 for adjusting the direction of the μ-TAS chip held by the chip holding portion 22 is provided on the rotary body 25, and the chip holding portion 22 for holding the μ-TAS chip is arranged on the direction switching gear 26.

Also, as mentioned above, the driving-side gear 33 is provided which meshes with the direction switching gear 26 which is rotatably provided with respect to the driving shaft 24b via the ball bearing 32 or the like. By driving a chip direction switching motor (not shown), the driving-side gear 33 rotates, the direction switching gear 26 which meshes with this gear rotates about a shaft D, and the chip holding portion 22 rotates. In addition, although switching by a gear (planet gear) has been described as the chip direction switching mechanism, for example, a configuration in which switching is made by rotating the chip holding portion with a magnet may be adopted.

As shown in FIG. 4B, the chip holding portion 22 is provided with the aperture 23. When the μ-TAS chip is mounted on the chip holding portion 22, the light from the light source 41 enters a measuring area of the μ-TAS chip through the aperture 23.

Additionally, a measurement position setting step according to the exemplary embodiment is performed before the μ-TAS chip is mounted on the chip holding portion 22. In this step, while the light from the light source 41 is introduced into the aperture 23, the rotary body 25 is rotated by a minute amount, and the value of light quantity received by the light-receiving unit 43 in each rotational position is detected. Also, as described later, when light value reaches a threshold value, which is set in advance, or more, or when the position of the rotary body where the quantity of light becomes maximum is determined, this position is used as the measurement position.

In addition, an encoder value detected by the encoder 24c when the rotary body 25 is rotated minutely is illustrated in FIG. 4B.

Figure 5:
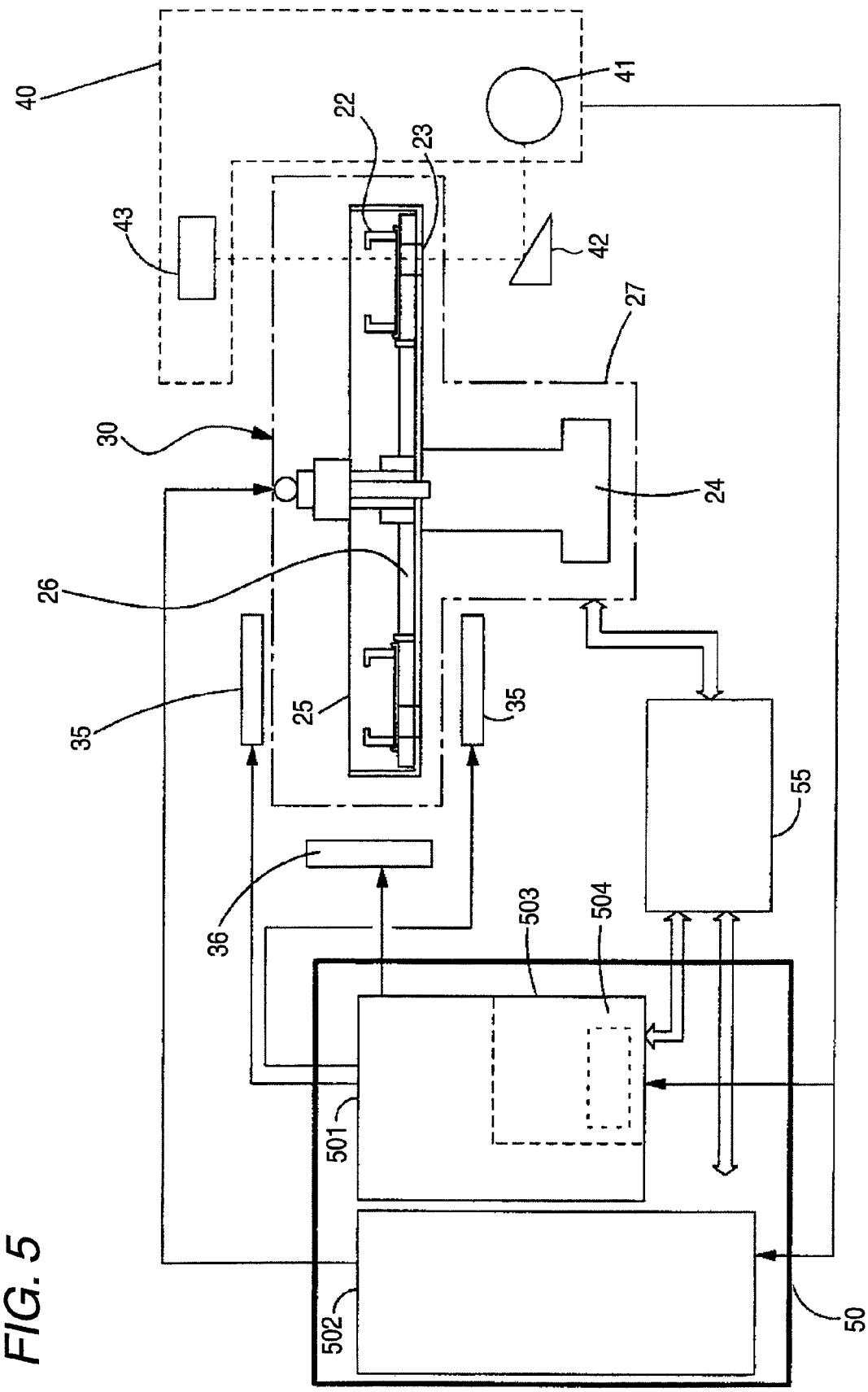
FIG. 5 is a block diagram showing a system configuration of the blood analysis apparatus according to the first embodiment of the invention.

FIG. 5 is a block diagram showing a system configuration of the blood analysis apparatus according to this embodiment.

In FIG. 5, a driving unit 27 is composed of the rotary body 25, the rotation driving mechanism 24 which rotationally drives the rotary body 25, the chip holding portion 22 for holding the μ-TAS chip, the direction switching gear 26 for switching the direction of the μ-TAS chip, the chip direction switching mechanism 30, and the like.

The chip holding portion 22 is provided with the aperture 23, and the light from the light source 41 of the measuring unit 40 is reflected by the reflecting mirror 42, passes through the aperture 23 (passes through the measuring area when the μ-TAS chip is mounted), and is received by the light-receiving unit 43.

Additionally, as mentioned above, the heating means 35 for controlling the ambient temperature of the μ-TAS chip or the rotary body 25, the temperature measuring means 36 for detecting the temperature of a driving unit or the like are provided.

The rotation driving mechanism 24 is controlled by the driving unit controller 55, and the driving unit controller 55 controls the rotation driving mechanism 24 in response to a driving command signal given from a controller 50, thereby rotationally driving the rotary body 25, or positioning the rotary body 25 in a given rotational position.

The controller 50 includes an initializing step control section 501 and a measuring step control section 502. The controller 50 sends a driving command signal to the driving unit controller 55 to control the rotation driving mechanism 24, and controls the heating means 35, the measuring unit 40, the chip direction switching mechanism 30 so as to control various steps for blood analytical processing.

In this embodiment, the measurement position setting step of determining the measurement position of the rotary body 25 where the rotary body 25 is rotated and the quantity of light passing through the aperture 23 becomes a threshold value (or a maximum quantity of light) or more is performed as one step in the initializing step control section 501 of the controller 50. In addition, the measurement position setting step may be performed any time as long as it is performed before a measurement liquid is measured.

Hereinafter, the absorbance measuring processing by the controller 50 and the driving unit controller 55 will be described.

First, the control of the rotation driving mechanism 24 by the driving unit controller 55 will be described.

Figure 6:
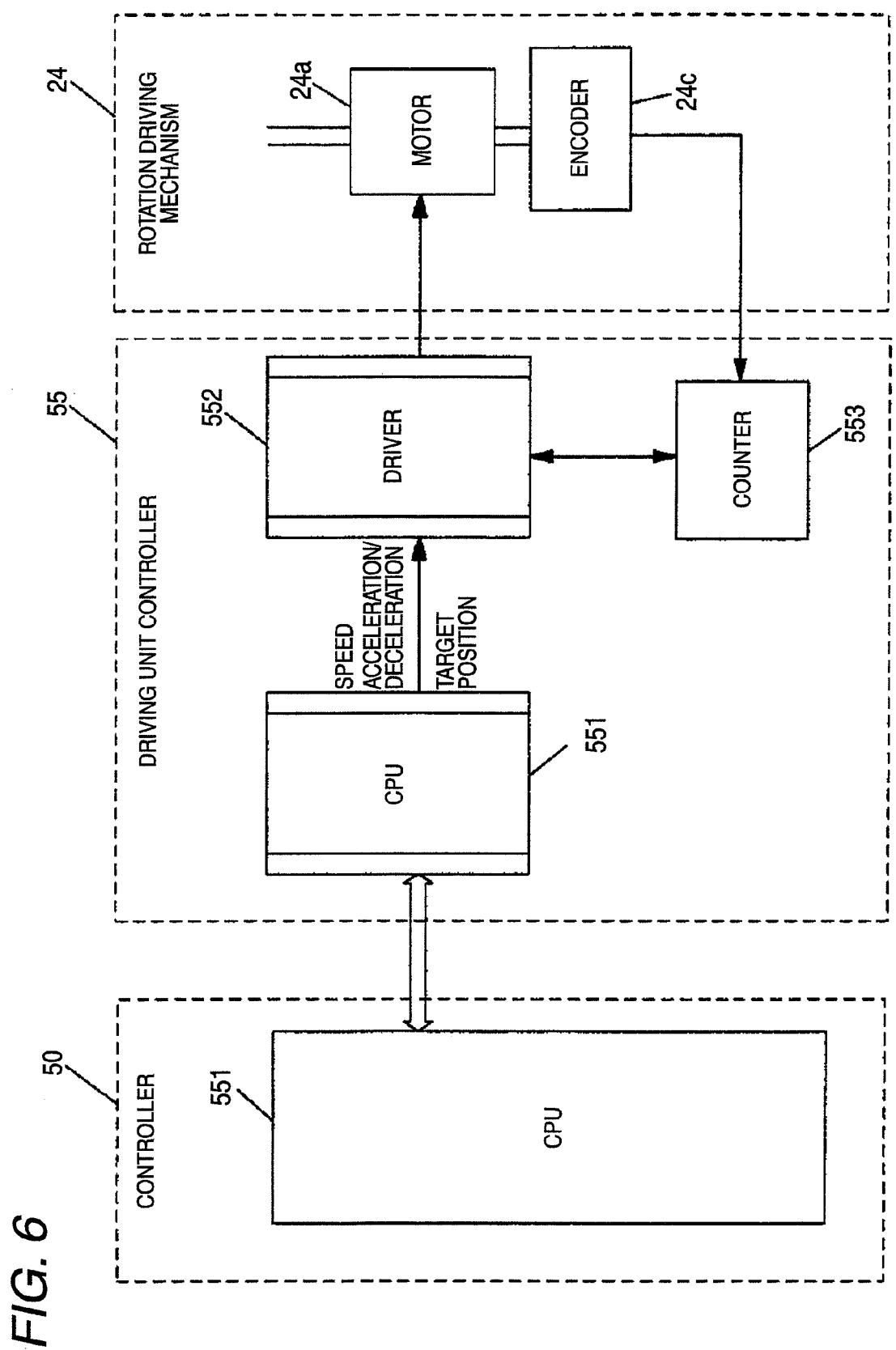
FIG. 6 is a block diagram showing a schematic configuration of a driving unit controller when an encoder motor is used.
Figure 7:
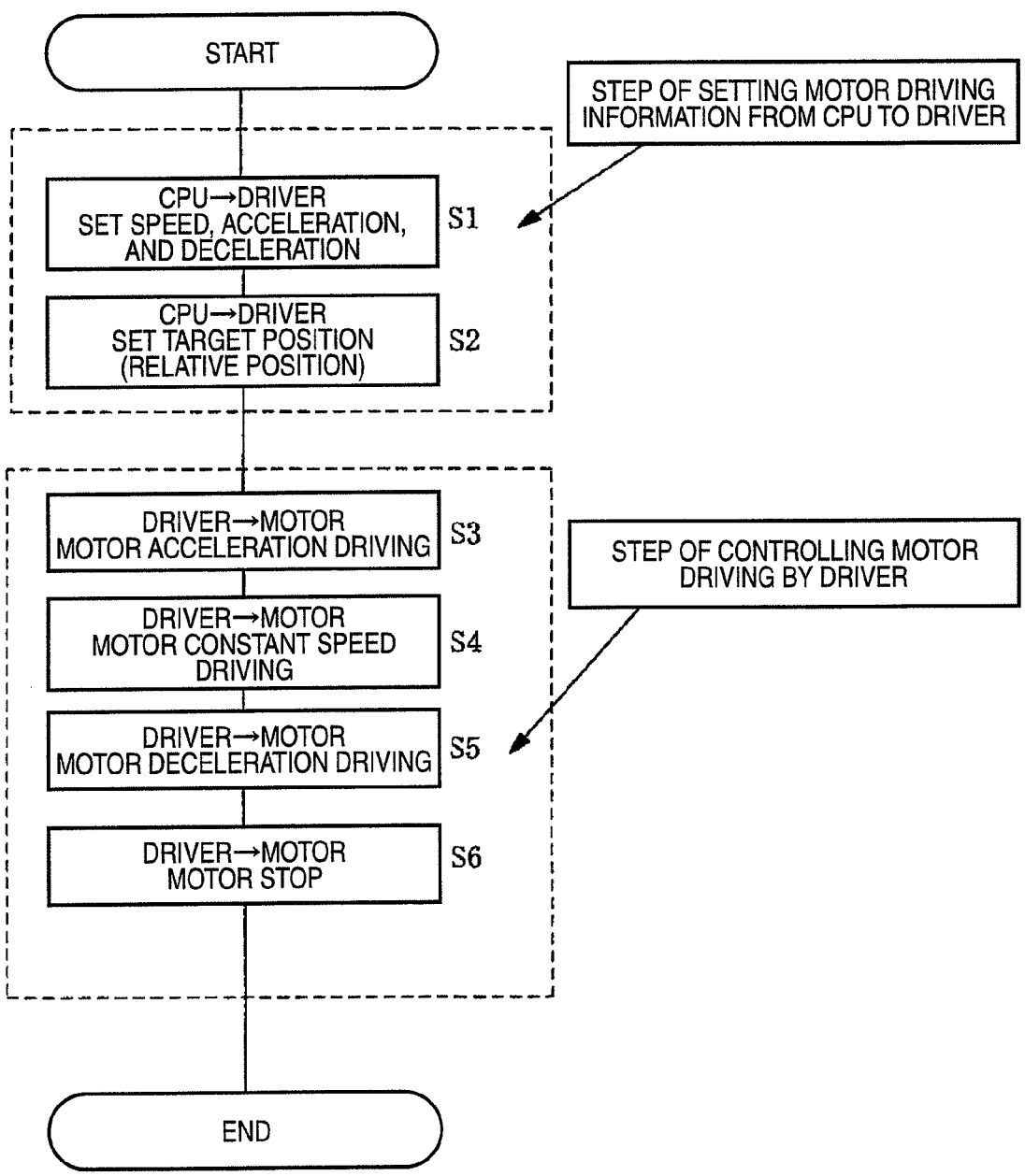
FIG. 7 is a flowchart showing the control processing in the driving unit controller when the encoder motor is used.

FIG. 6 is a block diagram showing the schematic configuration of the driving unit controller 55, and FIG. 7 is a flow-chart showing control processing in the driving unit controller 55. As shown in FIG. 6, the driving unit controller 55 is provided with a CPU 551 and a driver 552 for driving the centrifugal motor 24a, and the driver 552 communicates with a counter 553 in which a rotational position detected by the encoder 24c is set. In addition, the centrifugal motor 24a may be a DC motor, and a rotary shaft of the motor is provided with the encoder 24c for detecting a rotational position.

The driving control of the centrifugal motor 24a will be described with the flowchart of FIG. 7.

When the driving command of the motor 24a is given from the controller 50 to the CPU 551, the CPU 551 set motor driving information in the driver 552. That is, the CPU 551 sets the speed, acceleration, and deceleration of the motor 24a in the driver 552 (Step S1), and calculates and sets a target position (a relative position, i.e., a travel distance from a current position) where the motor 24a stops (Step S2). Here, the target position is given as follows.

Target Position=(Speed (rpm))×Rotation Time((second)/60)×Pulse Number

Here, the pulse number of one cycle of the encoder is about 1000, for example.

In addition, in the control of centrifugation driving, origin movement, and measurement position movement of the motor 24a (described later), even when the motor 24a is rotationally driven for centrifugation just because the "speed, acceleration and deceleration", "target position" being different, a driving command is given as a target position, and the motor 24a rotates by a given rotational frequency until it reaches the target position, and stops at the target position.

The driver 552 drives a motor on the basis of the "speed, acceleration and deceleration" and the "target position" which are given from the CPU 551.

That is, when data are given above, the driver 552 generates the acceleration, constant speed, and deceleration patterns of the motor 24a, perform acceleration driving, constant speed driving, and deceleration driving of the motor 24a on the basis of this acceleration and deceleration patterns, and stops the motor 24a in the target position (Step S3 to S6 of FIG. 7). Since the rotation of the motor is detected by the encoder 24c according to the rotation of the motor, and the rotational position of the motor is set in the counter 553, the driver 552 drives the motor 24a so that the rotational position of the motor 24a coincides with the acceleration and deceleration patterns and the constant speed pattern.

Although the case where a motor with an encoder is used as the motor has been described in FIGS. 6 and 7, a pulse motor (stepping motor) can also be used as the motor which drives the rotary body 25, instead of it.

Hereinafter, a case where the pulse motor is used as the centrifugal motor 24a will be described.

Figure 8:
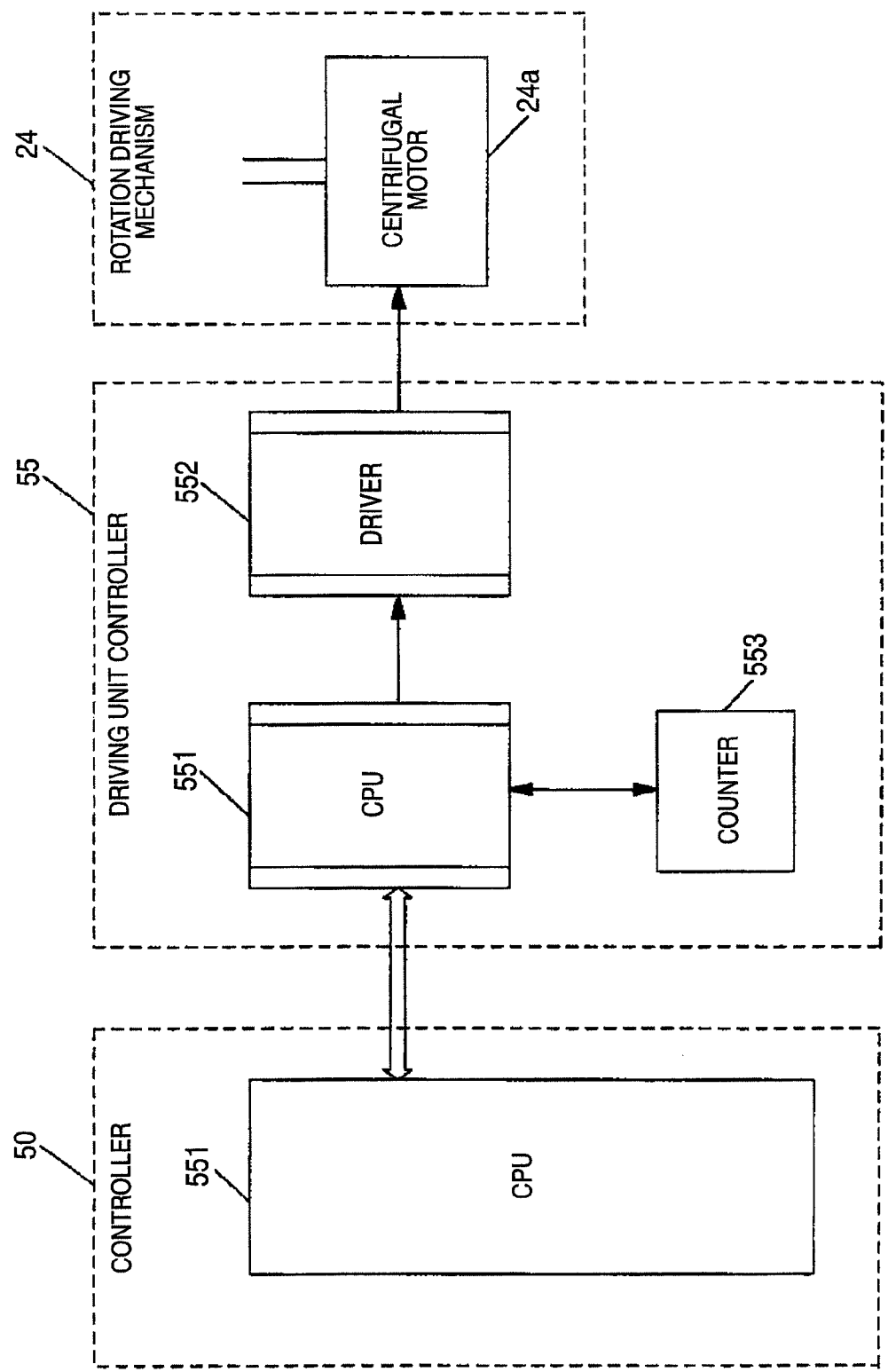
FIG. 8 is a block diagram showing a schematic configuration of the driving unit controller when a pulse motor is used.
Figure 9:
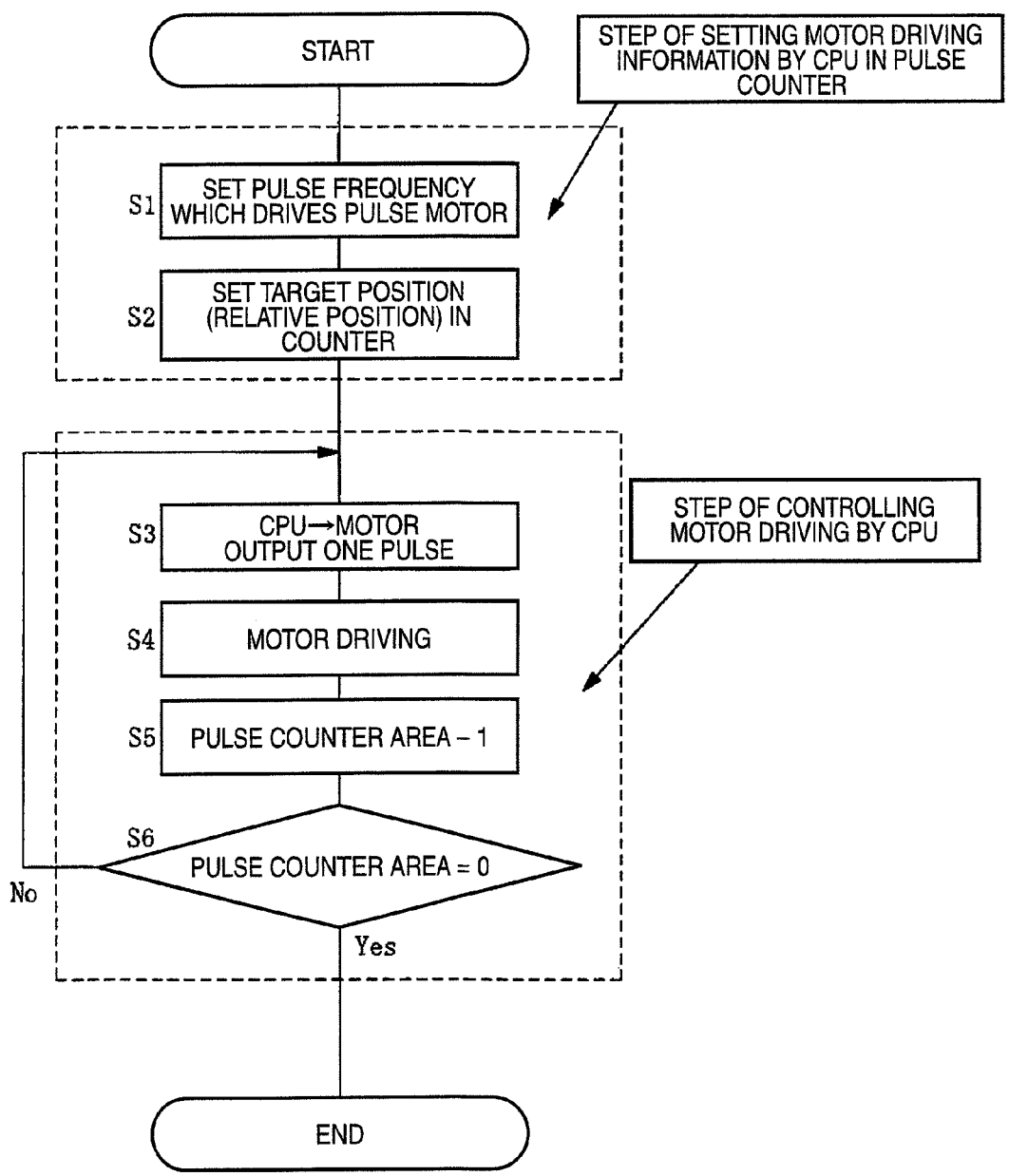
FIG. 9 is a flowchart showing the control processing in the driving unit controller when the pulse motor is used.

FIG. 8 is a block diagram showing the schematic configuration of the driving unit controller 55 when the pulse motor is used. FIG. 9 is a flowchart showing control processing in the driving unit controller 55.

As shown in FIG. 8, the driving unit controller 55 is provided with the CPU 551, the counter 553 in which the amount of driving is set, and the driver 552 which outputs a pulse signal for driving the centrifugal motor 24a (pulse motor).

In addition, the pulse motor is a motor which rotates by a constant angle with respect to one pulse, and the rotational angle is called a step angle. As the step angle is made smaller, resolution power becomes higher. For example, if the pulse motor which makes one rotation in 1000 pulses is used, the resolution power equal to that of the motor with an encoder (in a case where an encoder which outputs 1000 pulses in one rotation is used) can be obtained.

The driving control of the centrifugal motor 24a when the pulse motor is used will be described with reference to the flowchart of FIG. 9.

When a driving command of the motor 24a is given from the controller 50 to the CPU 551, the CPU 551 performs initialization setting such as the pulse rate (pulse frequency) setting of driving pulses supplied to the pulse motor 24a according to speed, acceleration, and deceleration (Step S1), and sets the target position (relative position) in the counter 553 (Step S2).

Here, the target position is set as follows similarly to the case where the motor with an encoder is used.

Target Position=(Speed (rpm)×Rotation Time(second)/60)×Pulse Number

For example, the step angle of the pulse motor is about 0.72° (5-phase pulse motor), and generated pulse frequency is about 10 kHz.

Thus, the pulse motor 24a is driven.

That is, one pulse is output at the above pulse rate set in the pulse motor 24a (Step S3). Then, if the motor 24a is driven, a value held in the counter 553 is reduced by one (Steps S4 and S5). Then, it is checked whether or not the value held at the counter 553 becomes 0. Then, if the value becomes 0, the driving of the motor is stopped, and if the value is not 0, the process returns to Step S3 and the above processing is repeatedly performed.

Next, the processing of absorbance measurement according to this embodiment will be described.

Figure 10:
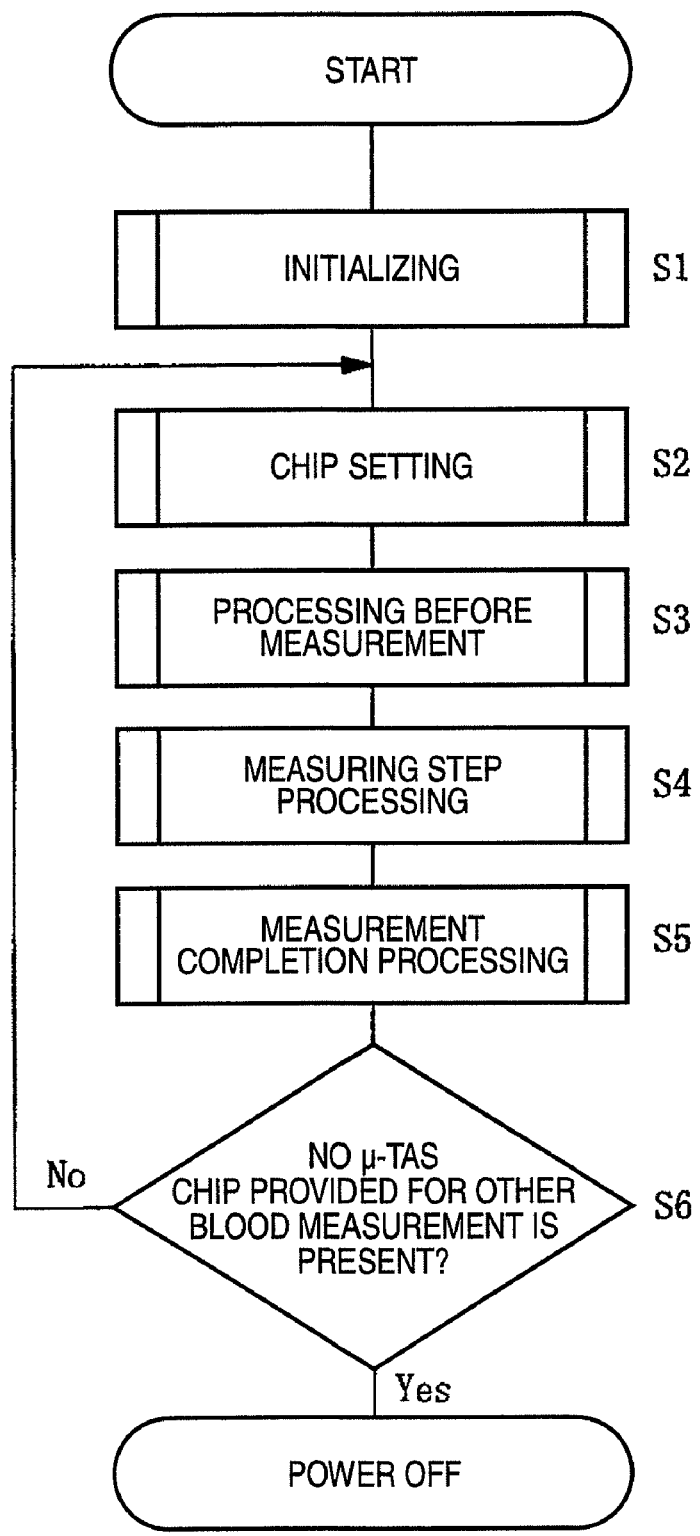
FIG. 10 is a schematic flowchart showing all steps of absorbance measurement of a measurement liquid held by a μ-TAS chip.

FIG. 10 is a schematic flowchart showing all steps of absorbance measurement of a measurement liquid held by a μ-TAS chip (hereinafter referred to as "chip").

First, initializing processing of the blood analysis apparatus is performed (Step S1). In this step, measurement position setting processing according to the exemplary embodiment (described later) is performed after incubation processing in which the measuring chamber 21 is heated to set the temperature of the chamber to a preset temperature.

Subsequently, the process proceeds to Steps S2 to S6, the chip is set in the chip holding portion 22 of the measuring chamber 21 (Step S2), and processing before measurement is performed (Step S3).

In the processing before measurement, weighing of a sample liquid, mixing of the sample liquid and a reagent, and the processing of delivering a measurement liquid to a measuring area is performed.

Next, the measuring step processing of measuring the absorbance of the measurement liquid within the measuring area is performed (Step S4), and measuring step completion processing is performed (Step S5). Then, if it is confirmed that there is no chip provided for other blood measurement (Step S6), the processing is ended. Additionally, if there is a chip provided for blood measurement, the process returns to Step S2 and the above processing is repeatedly performed.

Next, the above respective steps will be described in details.

(1) Initializing Step

Figure 11:
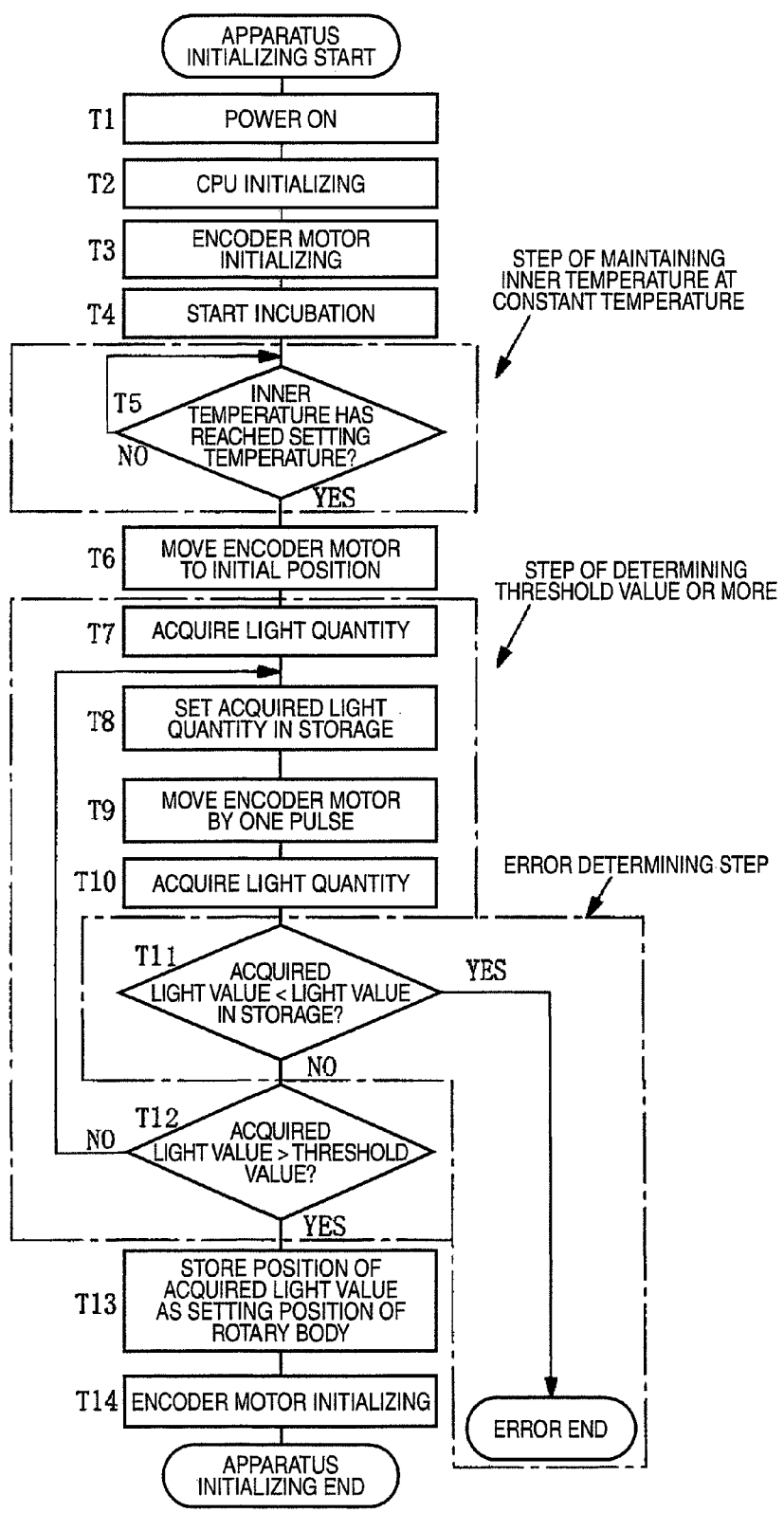
FIG. 11 is a flowchart (#1) showing the processing of an initializing step including a measurement position setting step according to the exemplary embodiment of the invention.

FIG. 11 is a flowchart showing the processing of the initializing step including the measurement position setting step according to the exemplary embodiment.

FIG. 11 shows a detailed flowchart of the initializing step which is performed before a chip is set in the chip holding portion (chip setting), and shows the processing in a case where the position of the rotary body where a measured light value becomes a threshold value or more is set to a measurement position.

In FIG. 11, apparatus initializing is started when a power source turned on.

First, a power source (not shown) is turned on by a power-on command, and feeding of power to the controller 50, the driving unit controller 55, and the like shown in FIG. 5 is started (Step T1).

Thereby, the initializing step control section 501 of the controller 50 initializes CPU which constitutes the controller 50, the driving unit controller 55, and the like, and initializes the motor 24a with an encoder in encoder motor initial processing (Steps T2 and T3).

In addition, a case where the motor 24a (hereinafter simply referred to as "encoder motor" or "motor") with an encoder described in FIG. 6 is used as the motor which drives the rotary body 25 will be described herein.

Next, incubation is started at Step T4, and the process proceeds to a step where the temperature of the measuring chamber 21 becomes constant.

That is, the initializing step control section 501 of the controller 50 shown in FIG. 5 starts a rise in temperature of the heating means 35 so that the inner temperature of the measuring chamber 21 becomes a preset temperature.

Thereafter, whether or not the inner temperature of the measuring chamber 21 has become a preset temperature is determined by the temperature measuring means 36 such as a thermistor or the like (Step T5).

If the inner temperature becomes a preset temperature, a measurement position setting part 503 of the initializing step control section 501 of the controller 50 performs measurement position setting step processing which will be described later.

First, the encoder motor 24a is moved to an initial position (Step T6). That is, the measurement position setting part 503 outputs a driving command that allows the encoder motor 24a move to the initial position, to the driving unit controller 55, and then the driving unit controller 55 drives the encoder motor 24a to move the motor to the initial position as mentioned above.

In addition, the initial position is a seek starting position which is set in advance. However, the position of the aperture 23 of the deflected rotary body 25 is often closer to a design position. Therefore, from the viewpoint that the location where the quantity of light of a threshold value or more is obtained is found at high speed, it is advantageous that the rotational position of the motor 24a is moved within a range (see FIG. 4A) of ±15° from a line segment which extends from the driving shaft 24b (before deflected) of the rotary body to the aperture 23 without finding a location where the quantity of light of a threshold value or more is obtained with an arbitrary position as a starting point.

Here, this position is referred to as an encoder motor light quantity acquisition design position, and this "design position" means a rotational position (design value) of the motor 24a where the light from a light source enters the aperture 23 of the chip holding portion 22 in case where the rotary body 25 is not deflected.

That is, the time that is taken until the position where quantity of light becomes a threshold value or more is determined can be shortened by moving the encoder motor to the encoder motor light quantity acquisition design position in advance. In addition, in the flowchart of FIG. 13 (described later), the encoder motor is moved to the encoder motor light quantity acquisition design position.

Figure 12:
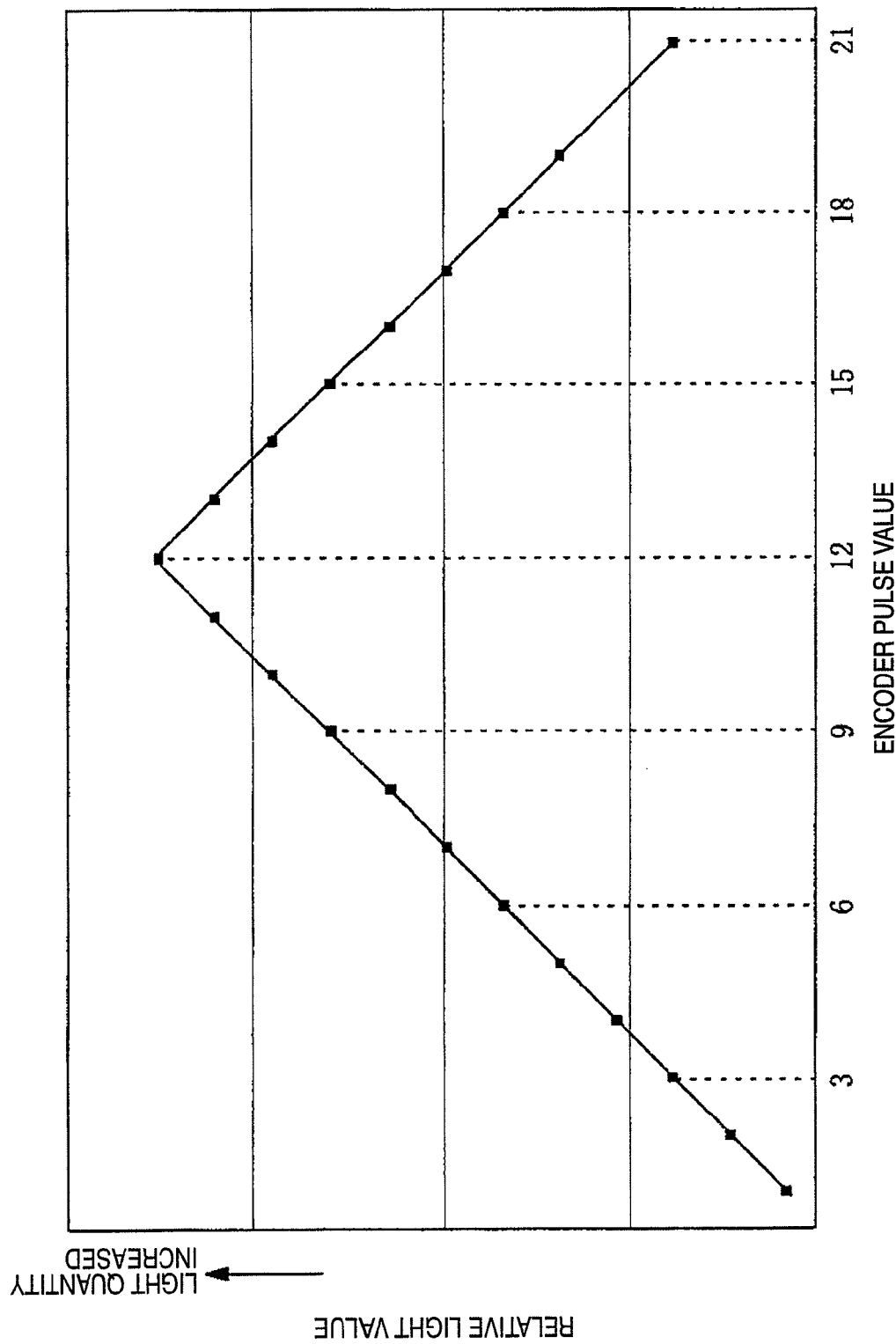
FIG. 12 is a view showing the relationship between an encoder pulse value and the quantity of light passing an aperture.

Hereinafter, the rotational position where the quantity of light which passes through the aperture 23 becomes a threshold value or more is found while the motor 24a is rotated little by little. FIG. 12 is a view showing the relationship between an encoder pulse value and the quantity of light passing through the aperture. In this example, when the encoder pulse value is 12, the light of quantity becomes maximum.

Here, in FIG. 12, description will be made assuming that the rotational position where the encoder pulse value is "9", for example, is the aforementioned light quantity acquisition design position.

After the encoder motor is moved to and stopped at the encoder motor light quantity acquisition design position, the quantity of light received by the light-receiving unit in the position is measured (Step T7). Then, the measured light value is stored in a storage 504 of the measurement position setting part 503 (Step T8).

Then, the encoder motor 24a is moved by one pulse, and the quantity of light received by the light-receiving unit is measured (Steps T9 and T10), and is compared with the light value previously stored in the storage 504 (Step T11).

In addition, in this example, assuming that the rotational direction of the encoder motor 24a in which the light value increases is known, the encoder motor 24a is moved in the direction. For example, in FIG. 12, the encoder motor 24a is moved in the direction in which the encoder motor pulse value increases, that is, to the right.

Accordingly, "acquired light value>previously stored light value" should be satisfied. If "acquired light value<previously stored light value" is established, the acquired light quantity does not reach the threshold value, but begins to decrease, or the motor movement direction is wrong. Accordingly, this case is ended as an error.

If "acquired light value≧previously stored light value" is established, it is determined whether or not the acquired light value is a threshold value or more (Step T12). If this light value is below this threshold value, the process returns to Step T8.

When the Steps T8 to T12 are repeatedly performed and the light value becomes the threshold value or more, movement of the encoder motor is stopped, and the rotational position of the encoder motor 24a at that time is stored as a setting position (Step T13).

Subsequently, initializing of the encoder motor 24a is performed (Step T14), and the apparatus initializing is ended.

In this embodiment shown in FIG. 11, the rotational position where the light value becomes the threshold value or more is determined while the rotary body 25 is rotated in a light quantity increasing direction which is known in advance. Thus, the position of the rotary body where the quantity of light of the threshold value or more is obtained can be obtained quickly.

Although the case where the rotational position where the measured light value becomes the threshold value or more is determined has been described in FIG. 11, the position of the rotary body where the measured light value becomes a maximum value and the threshold value or more may be determined.

Figure 13:
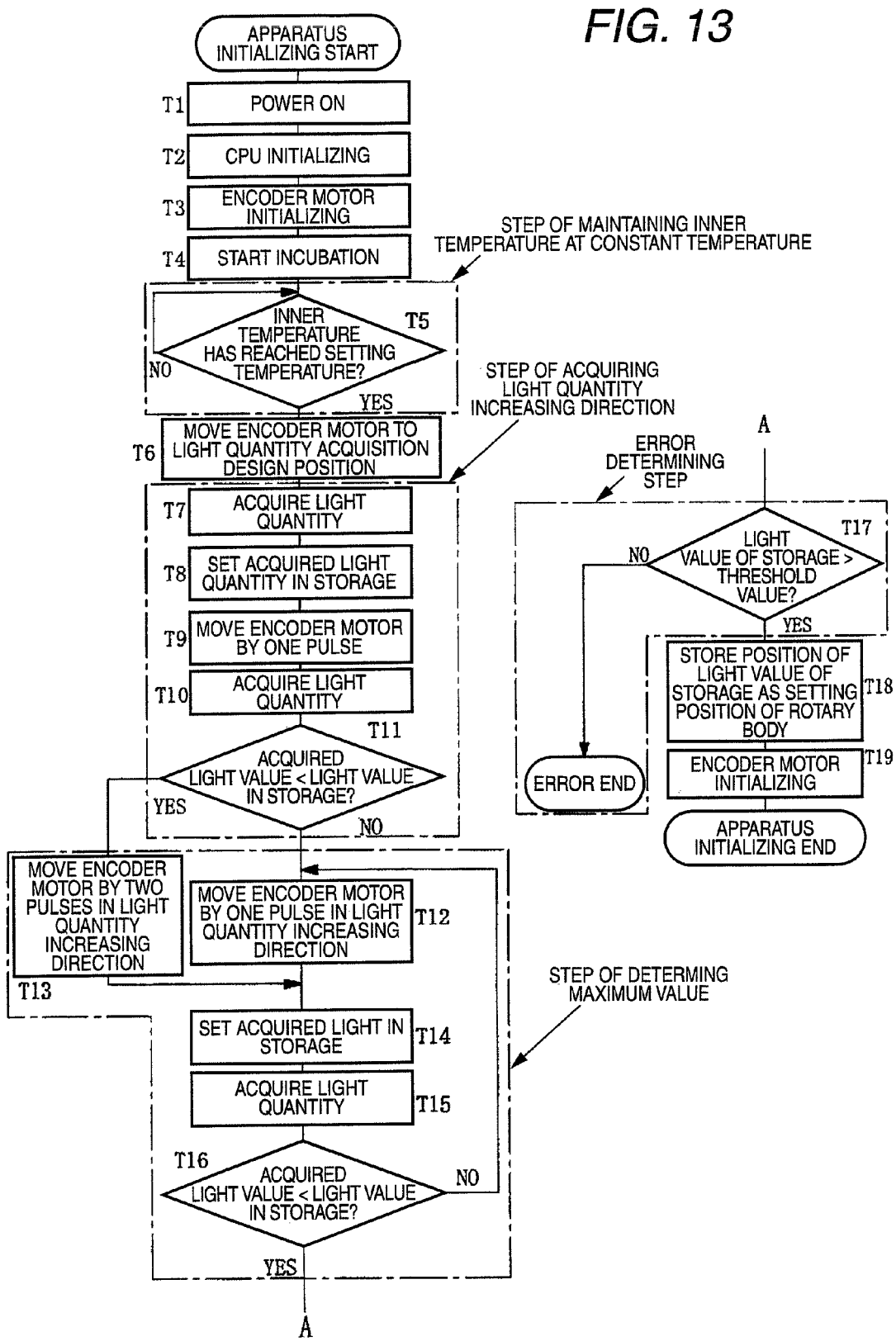
FIG. 13 is a flowchart (#2) showing the processing of the initializing step including the measurement position setting step according to the exemplary embodiments of the invention.

FIG. 13 shows a flowchart with regard to a case where the position of the rotary body where the determined light value becomes a maximum value is set to a measurement position.

The processing to Step T5 in FIG. 13 is the same as that of FIG. 11, and the processing after Step T6 will be described here.

In this embodiment, assuming that the rotational direction of the encoder motor in which the light value acquired by the light-receiving unit increases is not known, first, the rotational direction of the encoder motor in which the quantity of light increases is determined.

That is, the encoder motor 24a is moved to the aforementioned encoder motor light quantity acquisition design position (Step T6).

Next, the quantity of light received by the light-receiving unit is acquired, the acquired quantity of light is stored in the storage 504, and the encoder motor 24a is moved by one pulse (Steps T7 to T9).

Then, the quantity of light received by the light-receiving unit is acquired, and is compared with the above stored light value (Step T10 and T11). Then, whether or not the encoder motor rotates in the light quantity increasing direction is determined from the above comparison result.

If the above comparison result is "acquired light value>stored light value", the encoder motor 24a moves in the direction in which the light value increases. For example, if description is made with reference to FIG. 12, the encoder motor is moved in one direction of the rotary body, and the encoder pulse value is moved from "9" to "10". Then, "acquired light value>stored light value" is obtained.

Subsequently, the process proceeds to Step T12 where the encoder motor 24a is moved in a direction in which the quantity of light increases, i.e., by one pulse in this direction.

On the other hand, if "acquired light value<stored light value" is established in Step T11, the encoder motor 24a moves in a direction in which the light value decreases. Thus, the encoder motor 24a is moved in an opposite direction, i.e., by two steps in a direction in which the light value increases, (Step T13).

That is, in case of "acquired light value<stored light value", if description is made in the example of FIG. 12, the encoder pulse value is moved from "9" to "8", and the quantity of light in "8" is acquired.

In this case, it can be understood that the light quantity increasing direction is a direction in which the encoder pulse value changes from "9" to "10". Thus, if the encoder motor is moved by two pulses in the light quantity increasing direction (i.e., in a direction opposite to the direction in which the encoder motor has been rotated), the encoder pulse value can be moved from "8" to "10".

Subsequently, the rotational position of the encoder motor where the acquired light value becomes a maximum quantity of light is determined as follows.

First, the light value acquired in Step T10 is stored in the storage 504 in Step T14, and the quantity of light received by the light-receiving unit is acquired, and is compared with the stored light value (Steps T14 to T16). Then, if "acquired light value>stored light value" is established, it is found that the light value has not yet reached a maximum value. Thus, the process returns to Step T12, and the processing of the above Steps T12 to T15 is repeatedly performed.

If the above processing is repeatedly performed and "acquired light value<stored light value" is established, it is found that the acquired light value reaches a maximum value and begins to decrease beyond the maximum value. Thus, the light value stored in the storage is set to a maximum light value.

Description is made with reference to FIG. 12, for example. The encoder motor is moved in one direction, and the encoder pulse value moves in order of "10", "11", "12", and "13". Then, when the encoder pulse value is moved from "12" to "13", a change from "acquired light value>stored light value" to "acquired light value<stored light value" occurs. In this case, since it is found that the acquired light value reaches a maximum value and begins to decrease beyond the maximum value, the above encoder value "12" is set to a rotational position where a maximum light value is obtained.

Subsequently, the light value (maximum value) stored in the storage 504 is compared with the threshold value (Step T17).

Here, in case of "acquired light value<threshold value", it is found that the maximum value of the acquired light quantity does not reach the threshold value. In this case, the process is ended as an error. For example, in the example of FIG. 12, if the light value of the position where the encoder pulse value is "12" is below a threshold value, the light value does not exceed the threshold value, for example, due to the reason that the deflection of the rotary body is too large. Thus, this light value is determined as a fault.

Additionally, if the light value stored in the storage exceeds a threshold value, the rotational position of the encoder motor 24a where the light value exceeds the threshold value is stored as a setting position (Step T18).

Subsequently, initializing of the encoder motor 24a is performed (Step T19), and the apparatus initializing is ended.

(2) Chip Setting and Processing Before Measurement

After finishing the apparatus initializing, as shown in FIG. 1B, the cover 1a of the housing 1 of the blood analysis apparatus is opened, the µ-TAS chip is inserted into the chip insertion slot 1b of the measuring chamber, and the µ-TAS chip is mounted on the chip holding portion 22.

Figure 14:
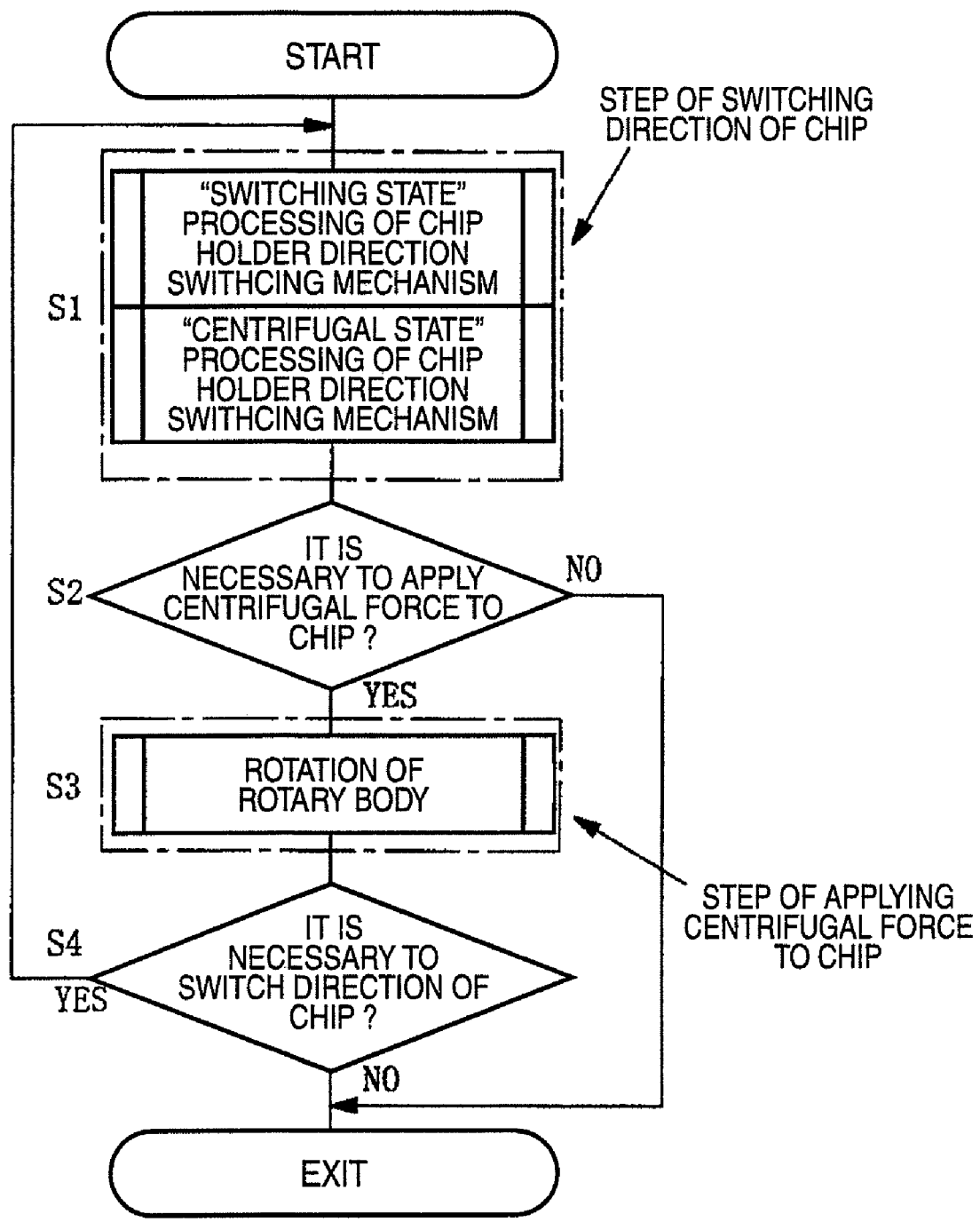
FIG. 14 is a schematic flowchart of processing steps before measurement.

After the chip setting, the processing before measurement is performed as shown in FIG. 14.

That is, in order to perform weighing of a sample liquid, mixing of the sample liquid and a reagent, and the processing of delivering a measurement liquid to a measuring area, the direction of a chip may be switched using the chip direction switching mechanism 30, as necessary. Also, if it is necessary to apply a centrifugal force to the chip, the rotary body 25 is rotated (Steps S1 to S3).

Figure 15:
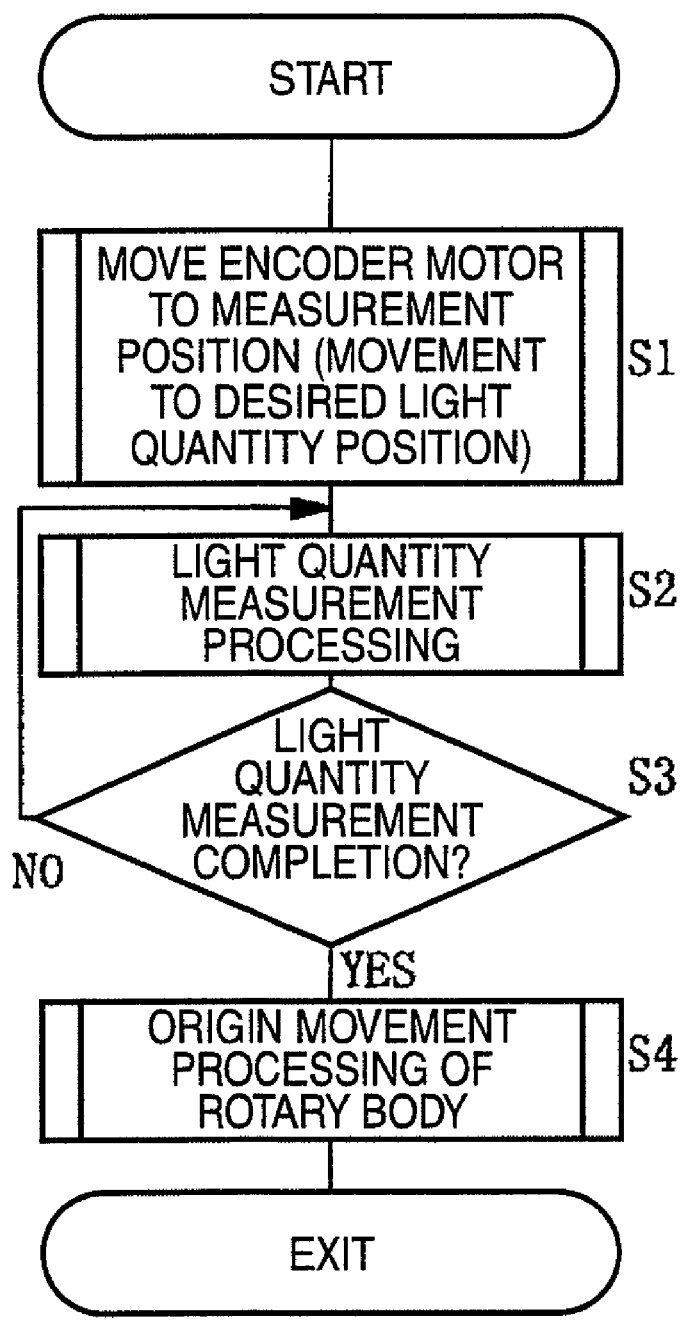
FIG. 15 is a schematic flowchart of a measurement processing step.

Then, if it is necessary to switch the direction of the chip to perform processing again, the process returns from Step S4 to Step S1, and the above steps are repeatedly performed (3) Measuring Processing Step When a measurement liquid for absorbance measurement is obtained in the above processing before measurement, absorbance measurement of this measurement liquid is be performed in the measuring step processing shown in FIG. 15.

That is, first, the encoder motor is rotationally moved to the encoder motor measurement setting position determined in the initializing step (Step S1).

Subsequently, absorbance measuring processing is performed (Step S1). That is, as described above, the light from the light source 41 enters the measuring area of the µ-TAS chip, then the light passing through the measuring area is received by the light-receiving unit 43, and thus absorbance is measured.

The measurement liquid held by the µ-TAS chip is measured in the measurement setting position where the light value of a threshold value or more is obtained. Thus, even if the rotary body is deflected due to a temperature change or the like, a reliable measurement result can be obtained.

After the end of measurement, origin movement processing of the rotary body 25 is performed within the measuring chamber, the rotary body 25 returns to the origin position, and the µ-TAS chip held by the chip holding portion 22 is taken out.

Otherwise, if no µ-TAS provided for blood measurement is present, the power source is turned OFF, and the process is ended.

As described above, the blood analysis apparatus according to the first embodiment is characterized in that a measurement position where a desired light quantity is obtained is determined and stored before the measurement liquid held by the µ-TAS chip is measured.

Particularly, in the blood analysis apparatus in which a heating means for heating the µ-TAS chip is provided to promote the reaction between blood and a reagent in the µ-TAS chip, the rotary body may be deflected due to thermal expansion or the like when the rotary body is heated by the heating means. Thus, in the blood analysis apparatus according to the first embodiment, the position where a desired light quantity is obtained is determined after the inside of the measuring chamber where the µ-TAS chip is arranged becomes a preset temperature. Thereby, it is possible to prevent displacement of setting position caused by deflection of the rotary body.

Also, a higher precision measurement result can be obtained by: determining the position where the maximum light value is obtained; storing this position; and setting the rotational position of the rotary body where the maximum light value is obtained as a measurement setting position.

Second Embodiment

Next, a second embodiment of the present invention will be described with reference to FIGS. 16 and 17.

Figure 16:
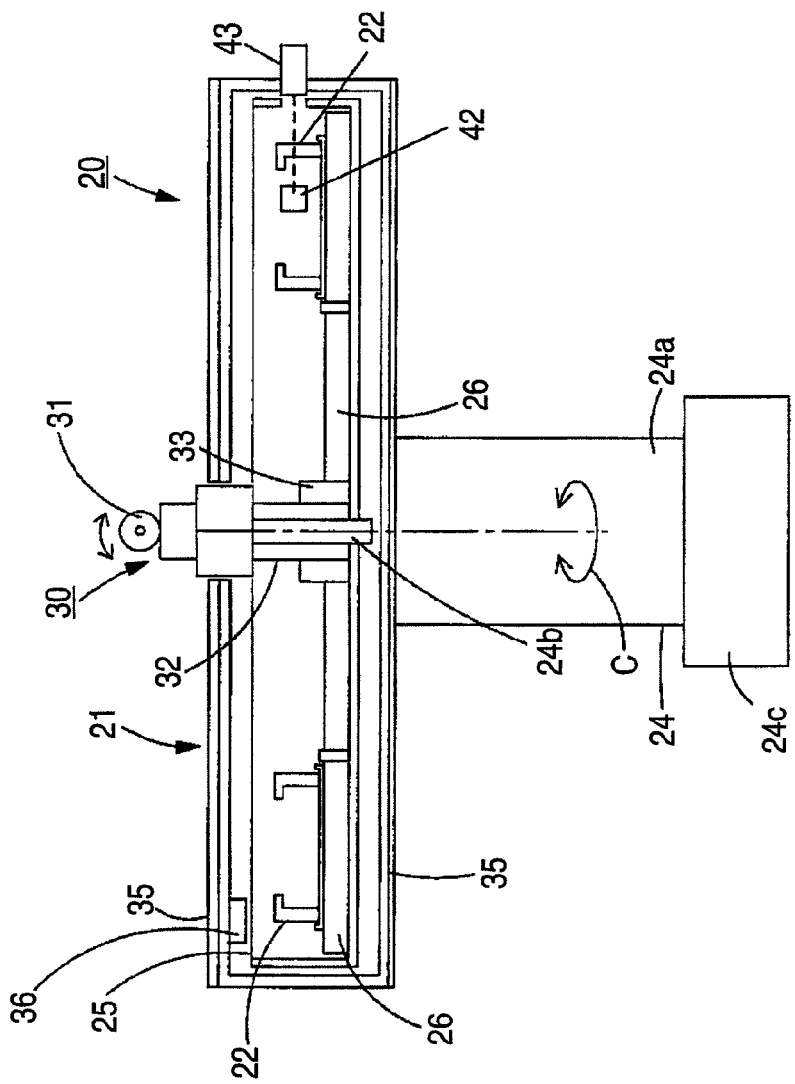
FIG. 16 is a cross-sectional view of a blood analysis apparatus according a second embodiment of the invention.
Figure 17:
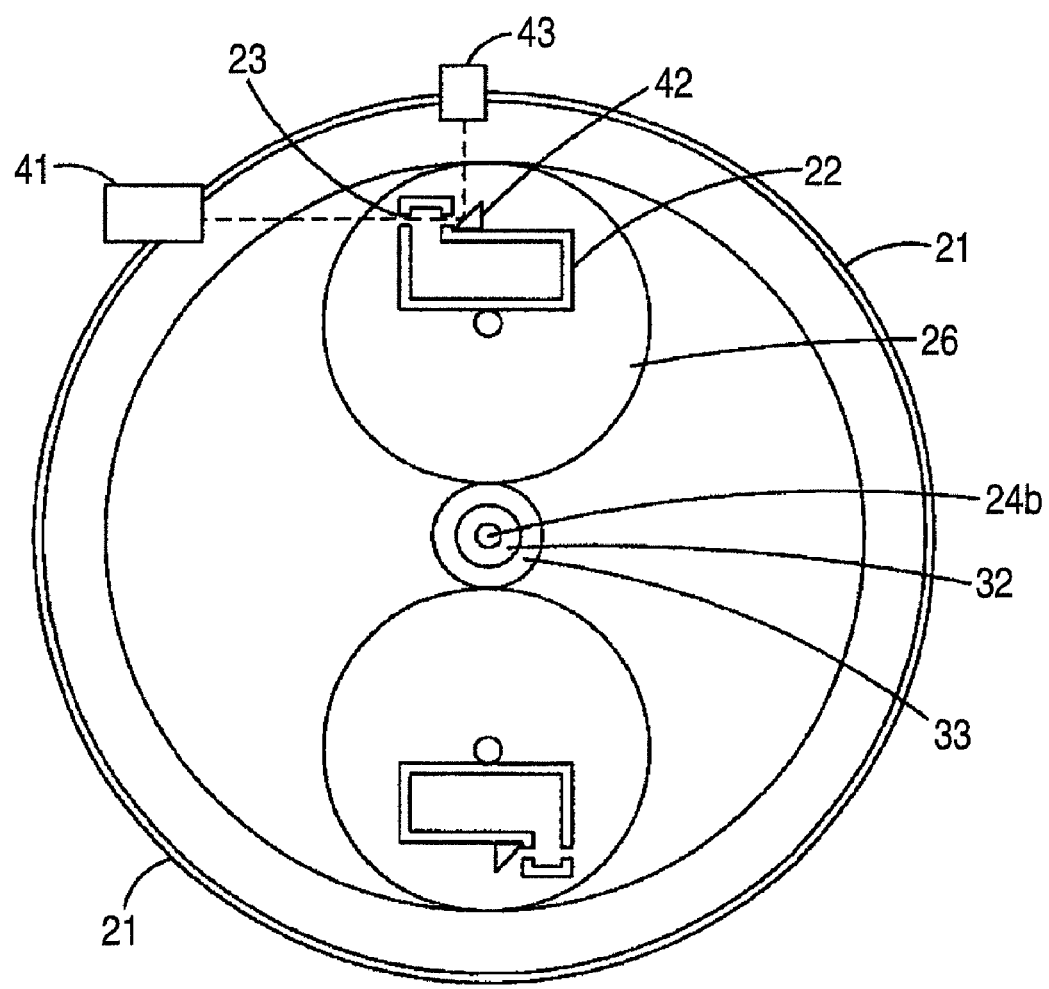
FIG. 17 is a view showing a rotary body of the blood analysis apparatus according to the second embodiment of the invention, when viewed from the chip holding side.

FIG. 16 shows a cross-sectional view of the blood analysis apparatus similarly to FIG. 3, and FIG. 17 is a conceptual diagram of the rotary body 25 when viewed from the chip holding portion similarly to FIG. 4A. However, in this embodiment, the positions of a light source and the light-receiving unit differ from those shown in FIGS. 3 and 4, and accordingly, the position of the aperture is also different.

That is, in this embodiment, as shown in FIG. 17, the aperture 23 is provided at a side wall portion of the chip holding portion 22, and the reflecting mirror 42 is provided on the chip holding portion 22 for holding the chip. Also, the light from the light source 41 enters the reflecting mirror 42 through the aperture 23 from a side direction of the rotary body 25, then is reflected by the reflecting mirror 42, and then enters the light-receiving unit 43 provided in the side direction of the rotary body 25 (FIG. 16 is a sectional view, and thus the above configuration is not shown in FIG. 16).

Other configurations are the same as those shown in FIG. 3. Here, as mentioned above, the measuring unit 20 has a hollow columnar measuring chamber 21, and the rotary body 25 is arranged within the measuring chamber 21. A centrifugal motor 24a of the rotation driving mechanism 24 is connected to the rotary body 25 via a driving shaft 24b, and the rotary body 25 is rotationally driven by the centrifugal motor 24a. Also, the centrifugal motor 24a is provided with an encoder 24c for detecting the rotational position of the motor.

As described above, a direction switching gear 26 is rotatably supported and provided at the bottom of the rotary body 25, and the chip holding portion 22 for holding the μ-TAS chip is provided on the gear 26.

Additionally, a planar heating means 35 for maintaining the temperature within the measuring chamber 21 at a constant temperature (for example, 37° C.) is provided in some regions of the top and bottom surfaces of the measuring chamber 21, and the temperature within the measuring chamber is controlled so as to become constant on the basis of the detection temperature by a temperature measuring means 36, such as a thermistor.

Additionally, the measuring unit 20 includes a chip direction switching mechanism 30 for adjusting the direction of the μ-TAS chip held by the chip holding portion 22 as mentioned above.

By driving the chip direction switching motor 31, the driving-side gear 33 rotates, then the direction switching gear 26 which meshes with this gear rotates, and then the chip holding portion 22 rotates. This makes it possible to switch the direction of the μ-TAS chip 60.

The configuration and operation of a control device in the blood analysis apparatus according to the second embodiment are as those of the first embodiment, and the control device can obtain the same effects as that of the blood analysis apparatus according to the first embodiment.

In addition, in this embodiment, since the chip holding portion 22 is provided with the reflecting mirror 42, the position of the reflecting mirror 42 also changes together with the deflection of the rotary body 25. For this reason, the blood analysis apparatus of this embodiment is affected by the deflection of the rotary body 25 more easily than the blood analysis apparatus in which the chip holding portion 22 is not provided with the reflecting mirror 42.

However, in this embodiment, the measurement setting position where the light value of a threshold value or more is obtained is determined. Accordingly, even if the position of the reflecting mirror 42 also changes together with deformation of the rotary body 25, a problem does not occur that the quantity of light which enters the aperture 23 from a light source decreases and thus measurement results vary.

Exemplary embodiments of the present invention have the following effects.

(1) The rotary body on which the chip holding portion is mounted is rotated before the measurement liquid is measured, and the position of the rotary body where the light value becomes a threshold value or more is determined, and is used as the measurement position. Thus, even if the rotary body deforms due to environmental temperature or the like, the position of the rotary body where a desired quantity of light required for measurement is obtained can be known. Therefore, it is possible to solve the problem that the quantity of light which enters the aperture from the light source is reduced and thus measurement results vary.

Particularly, the precision of measurement can be further improved by determining the measurement position where the light value of light received by the light-receiving unit becomes a maximum quantity of light.

(2) In the blood analysis apparatus having a heating means, it is considered that the deflection of the rotary body caused by temperature is large. However, the measurement position for which deformation caused by heating the heating means is taken into consideration can be determined by determining the measurement position after the ambient temperature of the chip holding portion becomes a predetermined temperature.

(3) The light value is determined as a fault when the light value does not reach the threshold value. Thereby, if deformation of the rotary body becomes too large and a desired quantity of light required for measurement is not obtained, it is possible to prevent the controller from infinitely seeking the position of the rotary body where the light value becomes the threshold value or more.

While the present invention has been shown and described with reference to certain exemplary embodiments thereof, it will be understood by those skilled in the art that various changes in form and details may be made therein without departing from the spirit and scope of the invention as defined by the appended claims. It is aimed, therefore, to cover in the appended claim all such changes and modifications as fall within the true spirit and scope of the present invention.

What is claimed is:

1. A blood analysis apparatus comprising:
   a driving unit comprising:
      a chip holding portion having an aperture which allows light to pass therethrough and holding a μ-TAS chip for holding a measurement liquid;
      a rotary body on which the chip holding portion is rotatably mounted;
      a rotation driving mechanism which rotates the rotary body; and
      a chip direction switching mechanism which changes a direction of the μ-TAS chip with respect to the rotary body;
   a measuring unit comprising:
      a light source which allows the light to enter the aperture; and
      a light-receiving unit which receives the light from the light source; and
   a controller which controls the rotation driving mechanism, the light source, and the light-receiving unit,
   wherein the controller comprises a measurement position setting part which determines a measurement position of the rotary body at which the measurement liquid is to be measured with the light from the light source,
   wherein, before the measurement liquid is measured, the measurement position setting part controls the rotation driving mechanism to rotate the rotary body in a state that the chip holding portion is fixed relative to the rotary body such that the chip holding portion is not rotated with respect to the rotary body and sets a rotational position of the rotary body where a light value of the light received by the light-receiving unit through the aperture is a threshold value or more, as the measurement position, and
   wherein the measurement position setting part determines the measurement position after heating the chip holding portion until an ambient temperature thereof reaches a certain temperature.

2. The blood analysis apparatus according to claim 1,
   wherein the measurement position setting part comprises a storage which stores quantities of light received by the light-receiving unit and positions of the rotary body each corresponding to one of the quantities of light,
   wherein the measurement position setting part seeks a position of the rotary body corresponding to a maximum quantity of light, and sets the position as the measurement position when a light value of the position is the threshold value or more.

3. The blood analysis apparatus according to claim 1, further comprising:
- a chamber in which the chip holding portion and the rotary body are arranged;
- a temperature measuring means provided in the chamber; and
- a heating means provided in the chamber, wherein the controller controls the heating means such that a certain temperature is measured by the temperature measuring means.

4. The blood analysis apparatus according to claim 1, wherein the measurement position setting part controls the rotation driving mechanism to repeatedly rotate the rotary body in one direction until the light value is the threshold value or more.

5. The blood analysis apparatus according to claim 4, wherein the measurement position setting part determines the light value as a fault when the light value does not reach the threshold value.

6. In a blood analysis apparatus comprising: a chip holding portion having an aperture which allows light to pass therethrough and holding a μ-TAS chip for holding a measurement liquid; a rotary body on which the chip holding portion is rotatably mounted; a light source; and a light-receiving unit, a method of setting a measurement position of the rotary body at which the measurement liquid is to be measured with the light from the light source, the method comprising:
- (a) rotating the rotary body in a state that the chip holding portion is fixed relative to the rotary body such that the chip holding portion is not rotated with respect to the rotary body to obtain a light value of light, said light being emitted from the light source and received by the light-receiving unit through the aperture;
- (b) setting a rotational position of the rotary body where the light value is a threshold value or more, as the measurement position; and
- (c) heating the chip holding portion until an ambient temperature thereof reaches a certain temperature, before steps (a) and (b).

7. The method according to claim 6, wherein step (b) comprises:
- (i) seeking a position of the rotary body corresponding to a maximum quantity of light; and
- (ii) setting the position as the measurement position when a light value of the position is the threshold value or more.

* * * * *